US009261498B2

(12) United States Patent
Sawyers et al.

(10) Patent No.: US 9,261,498 B2
(45) Date of Patent: Feb. 16, 2016

(54) BIOMARKER FOR SENSITIVITY TO MTOR INHIBITOR THERAPY IN KIDNEY CANCER

(75) Inventors: Charles L. Sawyers, New York, NY (US); George V. Thomas, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1525 days.

(21) Appl. No.: 11/886,444

(22) PCT Filed: Mar. 17, 2006

(86) PCT No.: PCT/US2006/009775
§ 371 (c)(1),
(2), (4) Date: Sep. 14, 2007

(87) PCT Pub. No.: WO2006/102111
PCT Pub. Date: Sep. 28, 2006

(65) Prior Publication Data
US 2009/0098537 A1 Apr. 16, 2009

Related U.S. Application Data

(60) Provisional application No. 60/662,649, filed on Mar. 17, 2005.

(51) Int. Cl.
C12Q 1/00 (2006.01)
C12Q 1/68 (2006.01)
G01N 1/00 (2006.01)
G01N 33/50 (2006.01)

(52) U.S. Cl.
CPC .......... *G01N 33/5091* (2013.01); *C12Q 1/6886* (2013.01); *C12Q 2600/106* (2013.01); *C12Q 2600/178* (2013.01); *G01N 2333/4703* (2013.01); *G01N 2333/4704* (2013.01)

(58) Field of Classification Search
None
See application file for complete search history.

(56) References Cited

U.S. PATENT DOCUMENTS

| 5,654,138 A * | 8/1997 | Lerman et al. ..................... 435/6 |
| 2005/0130193 A1* | 6/2005 | Luxon et al. ........................ 435/6 |
| 2006/0194211 A1* | 8/2006 | Burczynski et al. ............... 435/6 |

OTHER PUBLICATIONS

Saskashita et al. Expression of von Hippel-Lindau protein in normal and pathological human tissues. The Histochemical Journal 31:133-144, 1999.*
Jang et al. Clinical and Experimental Metastasis 15: 469-483, 1997.*
Bianco et al., "Loss of PTEN/MMAC1/TEP in EGF receptor-expressing tumor cells counteracts the antitumor action of EGFR tyrosine kinase inhibitors," Oncogene, 2003, 22:2812-2822.
Blume-Jensen et al., "Oncogenic kinase signalling," Nature, May 17, 2001, 411:355-365.
Burgering et al., "Cell cycle and death control: long live Forkheads," TRENDS in Biochemical Sciences, Jul. 2002, 27(7):352-360.
Chen et al., "Suppression of Growth of Renal Carcinoma Cells by the von Hippel-Landau Tumor Suppressor Gene," Cancer Research 55, 4804-7 Nov. 1, 1995.
Choe et al., "Active Matrix Metalloproteinase 9 Expression is Associated with Primary Glioblastoma Subtypes[1]," Clinical Cancer Research, Sep. 2002, 8:2894-2901.
Daneshmand et al., "A Pharmacodynamic Study of the Epidermal Growth Factor Receptor Tyrosine Kinase Inhibitor ZD1839 in Metastatic Colorectal Cancer Patients," Clinical Cancer Research, Jul. 2003, 9:2457-2464.
Datta et al., "The 104-123 Amino Acid Sequence of the B-domain of von Hippel-Landau Gene Product is Sufficient to Inhibit Renal Tumor Growth and Invasion,"Cancer Research 61, 1768-75 Mar. 1, 2001.
Davies et al., "Adenoviral Transgene Expression of MMAC/PTEN in Human Glioma Cells Inhibits Akt Activation and Induces Anoikis[1]," Cancer Research, Dec. 1, 1998, 58:5285-5290.
Davies et al., "Regulation of Akt/PKB Activity, Cellular Growth, and Apoptosis in Prostate Carcinoma Cells by MMAC/PTEN[1]," Cancer Research, Jun. 1, 1999, 59:2551-2556.
Druker et al., "Perspectives on the development of a molecularly targeted agent," Cancer Cell, Feb. 2002, 1:31-36.
Dutcher, "Mammalian target of rapamycin inhibition," Clin. Cancer Res., vol. 10, No Suppl., Sep. 15, 2004, pp. 6382S-6387S.
Ekstrand et al., "Amplified and rearranged epidermal growth factor receptor genes in human gliobastomas reveal deletions of sequences encoding portions of the N- and/or C-terminal tails," Proc. Natl. Acad. Sci. USA, May 1992, 89:4309-4313.
Ermoian et al., "Dysregulation of PTEN and Protein Kinase B is Associated with Glioma Histology and Patient Survival[1]," Clinical Cancer Research, May 2002, 8:1100-1106.
Feldkamp et al., "Signal transduction pathways and their relevance in human astrocytomas," Journal of Neuro-Oncology, 1997, 35:223-248.
Frederick et al., "Diversity and Frequencey of Epidermal Growth Factor Receptor Mutations in Human Glioblastomas," Mar. 1, 2000, Cancer Research, 60:1383-1387.
Gimm et al., "Differential Nuclear and Cytoplasmic Expression of PTEN in Normal Thyroid Tissue, and Benign and Malignant Epithelial Thyroid Tumors," American Journal of Pathology, May 2000, 156(5):1693-1700.
Gingras et al., "Regulation of translation initiation by FRAP/mTOR," Genes & Development, 2001, 15:807-826.
Gnarra et al., "Molecular Genetic Studies of Sporadic and Familial Renal Cell Carcinoma," Urologic Clinics of North America, vol. 20, 207-16, May 1993.
Gnarra et al., "Mutations of the VHL tumour suppressor gene in renal carcinoma," Nature Genetics, vol. 7, 85-90, May 1994.

(Continued)

*Primary Examiner* — Alana Harris Dent
(74) *Attorney, Agent, or Firm* — Gates & Cooper LLP

(57) ABSTRACT

The invention disclosed herein provides methods for the examination and/or quantification of biochemical pathways that are disregukted in pathologies such as cancer and to reagents and kits adapted for performing such methods. For example a correlation between VHL loss and mTOR inhibitor sensitivity in human kidney cancer cells is disclosed, indicating that VHL loss confers autonomous and angiogenic competitive advantages to such cells.

6 Claims, 11 Drawing Sheets

(56) References Cited

OTHER PUBLICATIONS

Gunaratnam et al., "Hypoxia Inducible Factor Activates the Transforming Growth Factor-$\alpha$ /Epidermal Growth Factor Receptor Growth Stimulatory Pathway in VHL -/- Renal Cell Carcinoma Cells*," Journal of Biological Chemistry, vol. 278, 44966-74, Nov. 7, 2003.

Gupta et al., "Local Recurrence in Head and Neck Cancer: Relationship to Radiation Resistance and Signal Transduction," Clinical Cancer Research, Mar. 2002, 8:885-892.

Harris, A.L., "Hypoxia—A Key Regulatory Factor in Tumour Growth," Nature Reviews Cancer, vol. 2, 38-47, Jan. 2002.

Hayashi et al., "Association of EGFR Gene Amplification and CDKN2 (p16/MTS1) Gene Deletion in Glioblastoma Multiforme," Brain Pathology, 1997, 7:871-875.

Hidalgo et al., "The rapamycin-sensitive signal transduction pathway as a target for cancer therapy," Oncogene, 2000, 19:6680-6686.

Hudson et al., "Regulation of hypoxia-inducible factor 1 alpha expression and function by the mammalian target of rapamycin," Mol. Cell. Biol., vol. 22, No. 20, pp. 7004-7014, Oct. 2002.

Iijima et al., "c-Raf/MEK/ERK Pathway Controls Protein Kinase C-mediated p70S6K Activation in Adult Cardiac Muscle Cells," The Journal of Biological Chemistry, Jun. 21, 2002, 277(25):23065-23075.

Ivan et al., "The von Hippel-Lindau tumor suppressor protein," Current Opinion in Genetics & Development 11, 27-34, 2001.

Kilic et al., "Intracranial Inhibition of Platelet-derived Growth Factor-mediated Glioblastoma Cell Growth by an Orally Active Kinase Inhibitor of the 2-Phenylaminopyrimidine Class[1]," Cancer Research, Sep. 15, 2000, 60:5143-5150.

Kondo et al., "The von Hippel-Lindau Tumor Suppressor Gene," Experimental Cell Research 264, 117-25 (2001).

Krieg et al., "Up-regulation of hypoxia-inducible factors HIF-1 alpha and HIF-2 alpha under normoxic conditions in renal carcinoma cells by von Hippel-Lindau tumor suppressor gene loss of function," Oncogene, vol. 19, 2000, pp. 5435-5443.

Laughner et al., "HER2 (neu) Signaling Increases the Rate of Hypoxia-Inducible Factor 1 $\alpha$ (HIF-1 $\alpha$) Synthesis: Novel Mechanism for HIF-1-Medicated Vascular Endothelial Growth Factor Expression" Molecular and Cellular Biology 21, 3995-4004, Jun. 2001.

Liotta et al., "Clinical Proteomics: Personalized Molecular Medicine," JAMA, Nov. 14, 2001, 286(18):2211-2214.

Liu et al., "PTEN/MMAC1 Mutations and EGFR Amplification in Glioblastomas," Cancer Research, Dec. 1, 1997, 57:5254-5257.

Lorimer et al., "Activation of extracellular-regulated kinases by normal and mutant EGF receptors," Biochimica et Biophysica Acta, 2001, 1538:1-9.

Malik et al., "Immunohistochemical Demonstration of Phospho-Akt in High Gleason Grade Prostate Cancer[1]," Clinical Cancer Research, Apr. 2002, 8:1168-1171.

Maxwell et al., "The tumour suppressor protein VHL targets hypoxia-inducible factors for oxygen-dependent proteolysis," Nature, vol. 399, 271-5, May 20, 1999.

Mischel et al., "Targeted Molecular Therapy of GBM," Brain Pathol, 2003, 13:52-61.

Moscatello et al., "Constitutive Activation of Phosphatidylinositol 3-Kinase by a Naturally Occurring Mutant Epidermal Growth Factor Receptor," The Journal of Biological Chemistry, Jan. 2, 1998, 273(1):200-206.

Mutter et al., "Molecular Identification of Latent Precancers in Histologically Normal Endometrium," Cancer Research, Jun. 1, 2001, 61:4311-4314.

Nagane et al., "Aberrant receptor signaling in human malignant gliomas: mechanisms and therapeutic implications," Cancer Letters, 2001, 162:S17-S21.

Neshat et al., "Enhanced sensitivity of PTEN-deficient tumors to inhibition of FRAP/mTOR," PNAS, Aug. 28, 2001, 98(18):10314-10319.

Nishikawa et al., "A mutant epidermal growth factor receptor common in human glioma confers enhanced tumorigenicity," Proc. Natl. Acad. Sci. USA, Aug. 1994, 91:7727-7731.

Ohh et al., "Ubiquitination of hypoxia-inducible factor requires direct binfing to the beta-domain of the von Hippel-Lindau protein," Nature Cell Biology, vol. 2, No. 7, Jul. 2000, pp. 423-427.

Perren et al., "Immunohistochemical Evidence of Loss of PTEN Expression in Primary Ductal Adenocarcinomas of the Breast," American Journal of Pathology, Oct. 1999, 155(4):1253-1260.

Perren et al., "Mutation and Expression Analyses Reveal Differential Subcellular Compartmentalization of PTEN in Endocrine Pancreatic Tumors Compared to Normal Islet Cells," American Journal of Pathology, Oct. 2000, 157(4):1097-1103.

Sawyers, "Rational therapeutic intervention in cancer: kinases as drug targets," Current Opinion in Genetics & Development, Feb. 2002, 12(1):111-115.

Schmidt et al., "Mutational Profile of the PTEN Gene in Primary Human Astrocytic Tumors and Cultivated Xenografts," Journal of Neuropathology and Experimental Neurology, Nov. 1999, 58(11):1170-1183.

Seagroves et al., "Two HIFs may be better than one," Cancer Cell, vol. 1, 211-3, Apr. 2002.

She et al., "Resistance to Gefitinib in PTEN-Null HER-Overexpressing Tumor Cells Can Be Overcome through Restoration of PTEN Function or Pharmacologic Modulation of Constitutive Phosphatidylinositol 3'-Kinase/Akt Pathway Signaling," Clinical Cancer Research, Oct. 1, 2003, 9:4340-4346.

Shi et al., "Signal Pathways Involved in Activation of $p70^{S6K}$ and Phosphorylation of 4E-BP1 following Exposure of Multiple Myeloma Tumor Cells to Interleukin-6*," The Journal of Biological Chemistry, May 2002, 277(18):15712-15720.

Smith et al., "PTEN Mutation, EGFR Amplification, and Outcome in Patients With Anaplastic Astrocytoma and Glioblastoma Multiforme," Journal of the National Cancer Institute, Aug. 15, 2001, 93(16):1246-1256.

Thomas et al., "Spontaneous Activation and Signaling by Overexpressed Epidermal Growth Factor Receptors in Glioblastoma Cells," Int. J. Cancer, 2003, 104:19-27.

Thomas et al., "Hypoxia-inducible factor determines sensitivity to inhibitors of mTOR kidney cancer," Nature Medicine, vol. 12, No. 1, Jan. 2006, pp. 122-127.

Vivanco et al., "The Phosphatidylinositol 3-Kinase-Akt Pathway in Human Cancer," Nature, Jul. 2002, 2:489-501.

Waldherr et al., "Monitoring antiproliferative responses to kinase inhibitor therapy in mice with 3'-deoxy-3'-18F-fluorothymidine PET," J. Nucl. Med., vol. 46, No. 1, Jan. 2005, pp. 114-120.

Watanabe et al., "Overexpression of the EGF Receptor and p53 Mutations are Mutually Exclusive in the Evolution of Primary and Secondary Glioblastomas," Brain Pathology, 1996, 6:217-224.

Wikstrand et al., "Cell Surface Localization and Density of the Tumor-associated Variant of the Epidermal Growth Factor Receptor, EGFRvIII[1]," Cancer Research, Sep. 15, 1997, 57(18):4130-4140.

Yakes et al., "Herceptin-induced Inhibition of Phosphatidylinositol-3 Kinase and Akt is Required for Antibody-mediated Effects on p27, Cyclin D1, and Antitumor Action[1]," Cancer Research, Jul. 15, 2002, 62:4132-4141.

Zhou et al., "PTEN Mutational Spectra, Expression Levels, and Subcellular Localization in Microsatellite Stable and Unstable Colorectal Cancers," American Journal of Pathology, Aug. 2002, 161(2):439-447.

International Search Report for International Application No. PCT/US2006/009775 filed on Mar. 17, 2006.

Canadian Office Action dated Dec. 20, 2014 for Canadian Patent Application No. 2,604,983.

Dancey, Janet E., "mTOR Inhibitors in Hematologic Malignancies", Clinical Advances in Hematology & Oncology, Jul. 2003, pp. 419-423, vol. 1, No. 7.

* cited by examiner

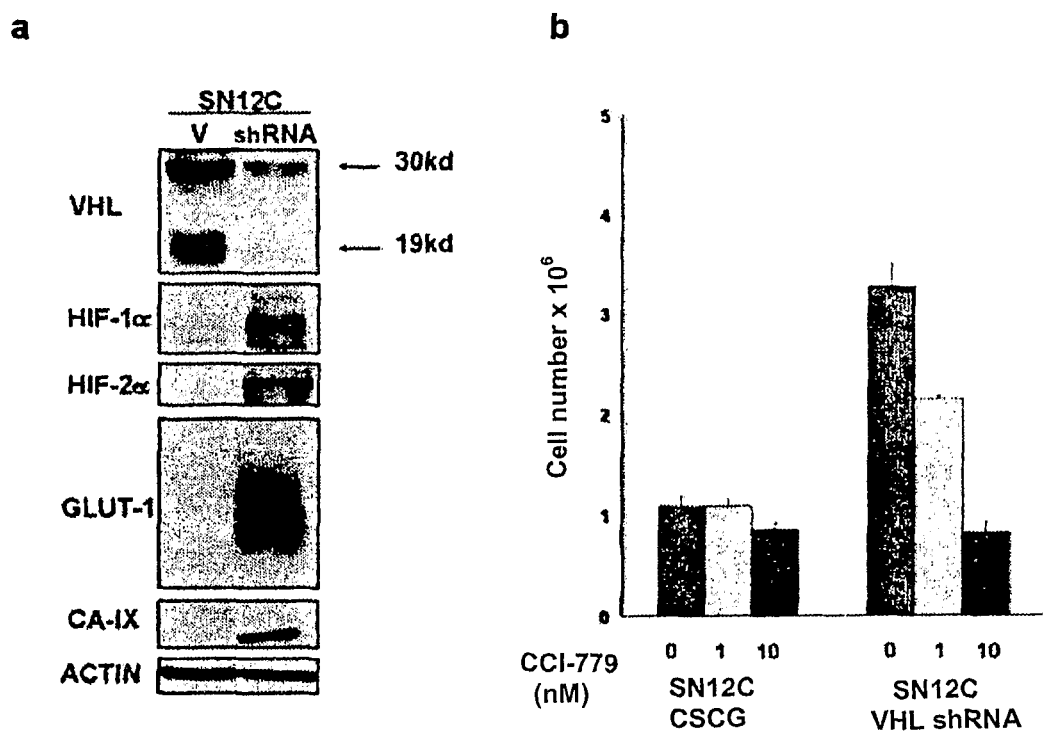
FIGS. 1A-B

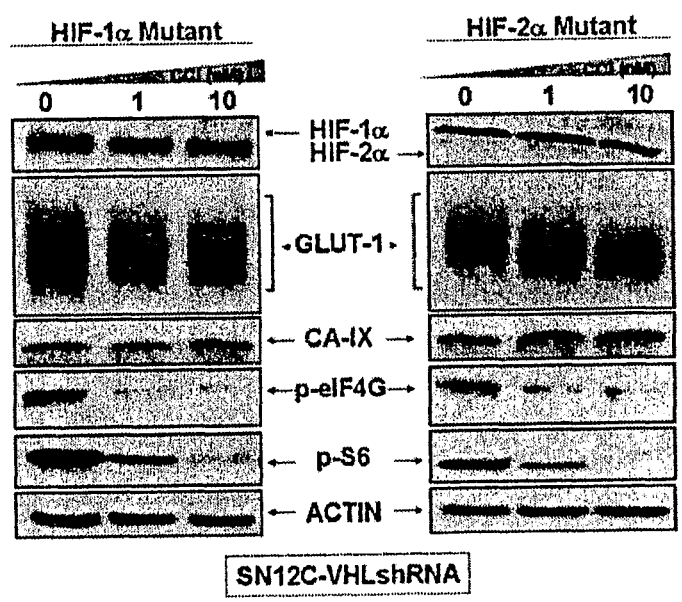
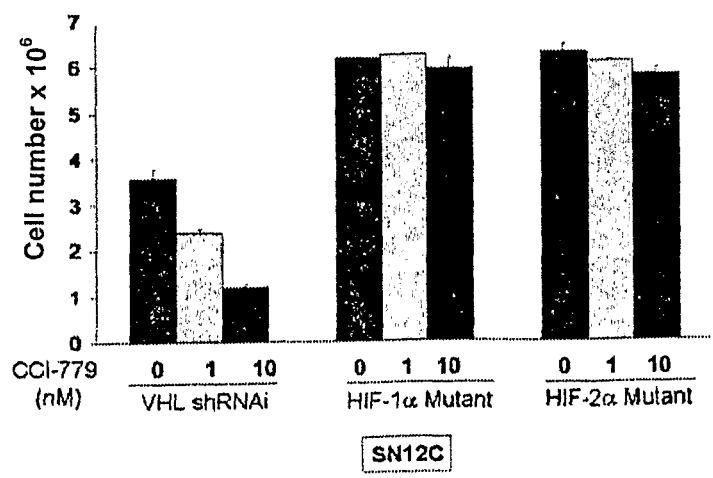
FIGS. 4A-B

US 9,261,498 B2

BIOMARKER FOR SENSITIVITY TO MTOR INHIBITOR THERAPY IN KIDNEY CANCER

RELATED APPLICATIONS

This application claims priority under Section 119(e) from U.S. Provisional Application Ser. No. 60/662,649 filed Mar. 17, 2005. This application is related to International Application Number PCT/US2004/037288 which is a continuation-in-part of U.S. patent application Ser. No. 10/701,490 filed Nov. 5, 2003, which claims the benefit of U.S. Provisional Application Ser. No. 60/423,777 filed Nov. 5, 2002, the contents of each of which are incorporated herein by reference.

STATEMENT OF GOVERNMENT SUPPORT

This invention was made with government support under DAMD17-02-1-0027 awarded by the United States Army, Medical Research and Materiel Command. The government has certain rights in the invention.

FIELD OF THE INVENTION

The present invention provides methods for the examination of biochemical pathways that are shown to be disregulated in pathologies such as cancer and to reagents adapted for performing these methods.

BACKGROUND OF THE INVENTION

Cancers are the second most prevalent cause of death in the United States, causing 450,000 deaths per year. One in three Americans will develop cancer, and one in five will die of cancer. While substantial progress has been made in identifying some of the likely environmental and hereditary causes of cancer, there is a need for additional diagnostic and therapeutic modalities that target cancer and related diseases and disorders. In particular, there is for a need a greater understanding of the various biochemical pathways that are involved in disregulated cell growth such as cancer as this will allow for the development of improved diagnostic and therapeutic methods for identifying and treating pathological syndromes associated with such growth disregulation.

With 32,000 new cases (representing an annual increase of 2%) and 12,000 cancer related deaths every year (see, e.g. Jemal, A. et al. Cancer statistics, 2004. CA Cancer J Clin 54, 8-29 (2004)), kidney cancers represent a major oncological therapeutic challenge. Standard chemotherapy agents have not been useful, and biologic agents such as interleukin-2 and interferon have shortcomings due to their toxicity profiles and the low meaningful response rates. Systemic chemotherapy produces few and only transient responses in patients with metastatic (i.e. advanced) kidney cancer. Given these limited treatment options, the results of the Phase II clinical trial using CCI-779 in patients with advanced kidney cancer, which found objective response rate of 7% and a disease stabilization rate of approximately 50% are intriguing, especially as there is no current molecular insight into the these group of patients who have mTOR dependent tumors (see, e.g. Atkins et al., J Clin Oncol 22, 909-18 (2004)). The parallels to the recent EGFR inhibitor trials in unselected lung cancer patients are striking. EGFR inhibitors (Iressa, Tarceva) have low, but consistent single agent objective response rates in refractory lung cancer.

Successful translation of kinase inhibitor compounds from the laboratory to the clinic depends on identifying subsets of patients most likely to benefit from them. A key to this is identifying kinase dependent tumors (see, e.g. Sawyers et al., Genes Dev 17, 2998-3010 (2003)). Most of the kinase inhibitors in clinical practice at present work on the paradigm of directly targeting the kinase mutation, e.g. BCR-ABL and Receptor Tyrosine Kinase (RTK) mutations/ligand overexpression, resulting in constitutive activation of downstream signaling molecules. These pathways can also be indirectly activated by loss of negative regulators, resulting in kinase activation, i.e. loss of PTEN and subsequent activation of the PI3K/AKT/mTOR cascade (see, e.g. Neshat et al., Proc Natl Acad Sci USA 98, 10314-9 (2001)). Prostate and brain tumors, which have tie highest mutation rates of PTEN, exhibited enhanced sensitivity to mTOR inhibitors, solidifying the proof of concept. Oncogenic dependence on this signal transduction pathway with subsequent inhibition of mTOR paralleled a "synthetic lethal" mode of action. Interestingly, CCI-779, a mTOR inhibitor, shows promising antitumor activity in advanced kidney cancers, with approximately 7% of patients showing objective response rates and disease stabilization in approximately 50% of patients (see, e.g. Atkins et al., J Clin Oncol 22, 909-18 (2004)). Based on preclinical data generated in prostate and brain tumors, this increased sensitivity could possibly be explained by the loss of the PTEN tumor suppressor gene. A potential drawback to this hypothesis however is the low incidence of somatic PTEN mutations in renal cancers. In addition, there are no known mutations of mTOR in kidney cancers.

As noted above, while researchers have identified a variety of genes and pathways involved in pathologies such as cancer, there is need in the art for additional tools to facilitate the analyses of the regulatory processes that are involved in disregulated cell growth. Moreover, an understanding of how the products of genes involved in disregulated cell growth interact in a larger context is needed for the development of improved diagnostic and therapeutic methods for identifying and treating pathological syndromes associated with growth disregulation. In particular, there remains a need to identify signal transduction events driving oncogenesis and to identify markers useful for assessing progression or inhibition of the oncogenic phenotype.

SUMMARY OF THE INVENTION

The clinical successes of molecularly targeted therapies so far have been in cancers with activating kinase mutations or conversely, when negative regulators of these kinases are lost. Interestingly, clinical response rates seen in solid tumors with mTOR inhibitors suggest presence of additional factors that may determine sensitivity to this class of molecularly targeted drugs. For example, CCI-779, a mTOR inhibitor, has shown selective anticancer properties in kidney cancers, though the mechanism for this is unknown. The instant disclosure shows how the loss of the Von Hippel Lindau (VHL) tumor suppressor gene plays a role in defining these clinical responses. The most common mutation in kidney cancers is loss of the VHL tumor suppressor gene, accounting for approximately 55-70% of cases. Loss of VHL results in stabilization of the transcription regulator, Hypoxia Inducible Factor complex (HIF). Using stable shRNAi targeting constructs, we characterize the prototypic functional knockdown of VHL. Knockdown of VHL results in HIF upregulation and we show that treatment with CCI-779 reduces HIF protein levels in these cells. We show a correlation between VHL loss and CCI-779 sensitivity in human kidney cancer cells, both in vitro and in vivo, indicating that VHL loss confers a cell autonomous and an angiogenic competitive advantage. We utilize the HIF dependent regulation of the glycolytic pathway to perform F-18 fluorodeoxyglucose-positron emission tomography (FDG-PET) and show how this can be clinically used to both select patients and monitor treatment efficacy. We perform rescue experiments by overexpressing mutant forms of HIF1α and HIF2α (which are no longer regulated by VHL), that results in reversal of the sensitivity to CCI-779. This finding suggests a novel mechanism of kinase dependency that is contingent on the translation of a molecule responsible for driving an oncottanscriptome program. The translational rheostat in this case is mTOR and the oncogenic molecule, HIF and predicts for a high therapeutic index. These data illustrate how the translation of an effector molecule promotes reliance on a specific oncogenic pathway leading to kinase dependency and offers new opportunities to broaden the therapeutic scope of kinase inhibitors. For example, an understanding of this relationship can be clinically used to both select patients and monitor treatment efficacy. Certain aspects of this invention are disclosed in Sawyers et al., Nat Med. 2006 January; 12(1):122-7, Epub 2005 Dec. 11, the contents of which are incorporated by reference.

All prior knowledge of the VHL/HIF pathway is based on biochemical data and genomic analysis, which are not currently feasible as a clinical screening tool. The invention disclosed herein provides a novel set of immunohistochemical, immunoblotting and positron emission tomography (PET) reagents that can serve as biomarkers to identify the loss of VHL an the subsequent activation of the HIF pathway. At present, there is no assay described in the art that allows artisans to identify the activation of this pathway in routinely processed samples (to include blood, serum, tissue) from patients with kidney cancer. These reagents identify coordinate regulation of the VHL/HIF-1α/HIF-2α/GLUT-1/CA-IX (CA9) and VEGF activation in response to the loss of the VHL tumor suppressor gene. Since specific kinase inhibitors that target this pathway are currently in development and since this mutation is common in kidney cancer, it is an extremely important clinical tool for selecting patients for appropriate therapy.

Currently, there is no available assay described in the art that allows one to assess the activation state of this pathway in routinely processed (formalin fixed, paraffin embedded) patient biopsy and resection samples as well as in PBMCs and serum. Consequently, the utility of the disclosed detection system is: (i) it can be used to determine the loss of VHL and the subsequent activation of HIF-1 and -2α and its downstream targets, GLUT-1, CA-IX (CA9) and VEGF on routinely processed patient samples, to include serum, peripheral blood mononuclear leukocytes (pbmc) and tissue samples; (ii) Activation of this pathway can be detected using F-18 fluorodeoxyglucose-positron emission tomography (FDG-PET); and (iii) this information can be used to select patients for therapy with targeted pathway inhibitors.

The invention can be practiced for example by: i) performing immunohistochemical analysis on routinely processed patient biopsy samples ii) performing immunoblotting analysis on PBMCs and ELISA on serum samples; and iii) performing FDG-PET scans on patients. The results of these assays can be used as criteria for inclusion in clinical trials and to assess outcome differences in patients in which this pathway is deregulated. The mechanism of the invention has been examined in human cancer cell lines, human cancer cell pellets and mouse xenograft (bearing human cancer cell lines) tumors. These results demonstrate clear coordinate regulation of HIF-1α and HIF-2α p with GLUT-1, CA-IX (CA9) and VEGF and their association with VHL loss.

VHL is lost in the majority of kidney cancers as well as certain adrenal, brain and ophthalmologic cancers. In addition, the HIF-1α and HIF-2α pathway is dysregulated in many other cancers. Therefore the ability to identify the activation state of this pathway, select patients who will benefit most from the inhibitors targeting this pathway and to monitor treatment efficacy is a valuable diagnostic test for kidney cancers as well as other cancers characterized by VHL loss associated disregulated cell growth. This is also extremely valuable for future analysis of new inhibitors that target this pathway.

The invention disclosed herein has a number of embodiments. One embodiment of the invention is a method for identifying a mammalian tumor cell (e.g. a kidney cancer cell) that is likely to respond, or is responsive to an mTOR polypeptide inhibitor, the method comprising examining the mammalian tumor cell for an at least 50% decrease in the expression of the Von Hippel Lindau (VHL) tumor suppressor protein in the mammalian tumor cell as compared to a control cell of the same cellular lineage as the mammalian tumor cell; wherein an at least 50% decrease in the expression of the Von Hippel Lindau (VHL) tumor suppressor protein identifies the mammalian tumor cell as likely to respond or responsive to an mTOR polypeptide inhibitor.

Another embodiment of the invention is a method for identifying a mammalian tumor cell that is likely to respond, or is responsive to an mTOR polypeptide inhibitor, the method comprising examining the mammalian tumor cell for expression of a Von Hippel Lindau (VHL) tumor suppressor protein having a deletion, substitution or insertion mutation; wherein these types of mutations in the Von Hippel Lindau (VHL) tumor suppressor protein identifies the mammalian tumor cell as likely to respond or responsive to an mTOR inhibitor.

Yet another embodiment of the invention is a method of monitoring the efficacy of an mTOR polypeptide inhibitor in the treatment of a mammalian tumor having a decrease in the expression of the Von Hippel Lindau (VHL) tumor suppressor protein (SEQ ID NO: 1), the method comprising examining cells in a biological sample for an at least 10% amount decrease in HIF-1α and/or HIF-2α polypeptide levels in a test cell from the mammalian tumor that has been exposed to the mTOR polypeptide inhibitor as compared to a cell from the mammalian tumor that has not been exposed to the mTOR polypeptide inhibitor; wherein an at least 10% amount decrease in HIF-1α and/or HIF-2α polypeptide levels in the test cell provides evidence that the mTOR polypeptide inhibitor is efficacious in the treatment of the mammalian tumor.

Embodiments of the invention also provide methods for fabricating articles of manufacture including probes, sets and kits. In one such embodiment of the invention, a kit contains a probe useful for sensing a HIF-1 and/or Von Hippel Lindau (VHL) tumor suppressor polynucleotide or polypeptide is provided. The kit typically includes a container, a label and a probe as described above. The typical embodiment is a kit including a container and, within the container, at least one probe and instructions for using these analyte sensing materials.

Other objects, features and advantages of embodiments of the present invention will become apparent to those skilled in the art from the following detailed description. It is to be understood, however, that the detailed description and specific examples, while indicating embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIGS. 1A-1E. Effects of VHL knockdown on sensitivity to CCI-779. (a) Immunoblotting of lysates derived from shRNA and control (empty vector, V) in SN12C, using antibodies against VHL (both isoforms detected), HIF-1α, HIF-2α, GLUT-1, CA-IX and β-Actin (as a loading control). (b) SN12C-CSCG and SN12C-VHLshRNA cells ($1 \times 10^5$) were cultured in 10% serum rich media, in the presence of vehicle, 1 or 10 nM of CCI-779 for 5 days. Cell growth was measured by cell counts (n=3). Similar results were seen with ACHN-CSCG and ACHN-VHL shRNA cells. (c) SN12C-CSCG (C1) and SN12C-CSCG shVHL RNA (C2) cells were injected into SCID mice at a dose of $1 \times 10^6$ cells per mouse (n=30). When tumor volume reached 150 mm$^3$, mice were randomized to daily treatment with vehicle or 0.1 mg/kg of CCI-779. The change in tumor volume is plotted. Phosphorylated-S6 protein in SN12C-CSCG and SN12C-VHL shRNA xenograft tumors treated with vehicle or 0.1 mg/kg of CCI-779 was measured by immunoblot C3 and C4). Equal loading verified by actin immunoblots. (d) Stable VHL knockdown in ACHN cells resulted in similar HIF-1α upregulation and enhanced sensitivity to CCI-779. (e) Schematic of shRNA-expressing lentivirus directed against VHL in pCSCG vector.

FIGS. 4A-4C. Rescue of CCI-779 growth suppression by HIF-1-α and HIF-2-α prolyl hydcroxylase mutants. SN12C-CSCG-VHLshRNA cells stably infected with the prolyl hydroxylation defective cDNA mutants p-Babe-puro-HA-HIF-1α (P564A), HIF-2α (P405A; P531A) or backbone vector were treated with CCI-779 or vehicle and harvested 24 hours later. (a) Lysates were subjected to immunoblotting for HIF-1α, HIF-2α, GLUT-1, CA-IX, p-eIF4G, p-S6 and β-Actin as loading control. (b) SN12C-VHLshRNA, SN12C-VHLshRNA-HIF-1α mutant, SN12C-VHLshRNA-HIF-2α mutant cells ($1 \times 10^5$) were cultured in 10% serum rich media, in the presence of vehicle, 1 or 10 nM of CCI-779 for 5 days. Cell growth was measured by cell counts (n=3). (c) SN12C-VHLshRNA-HIF-2α mutant cells were injected into SCID mice at a dose of $1 \times 10^6$ cells per mouse (n=16). When tumor volume reached 150 mm$^3$, mice were randomized to daily treatment with vehicle or 0.1 mg/kg of CCI-779. The fold change in tumor volume is plotted.

DETAILED DESCRIPTION OF THE INVENTION

Figure 1C:
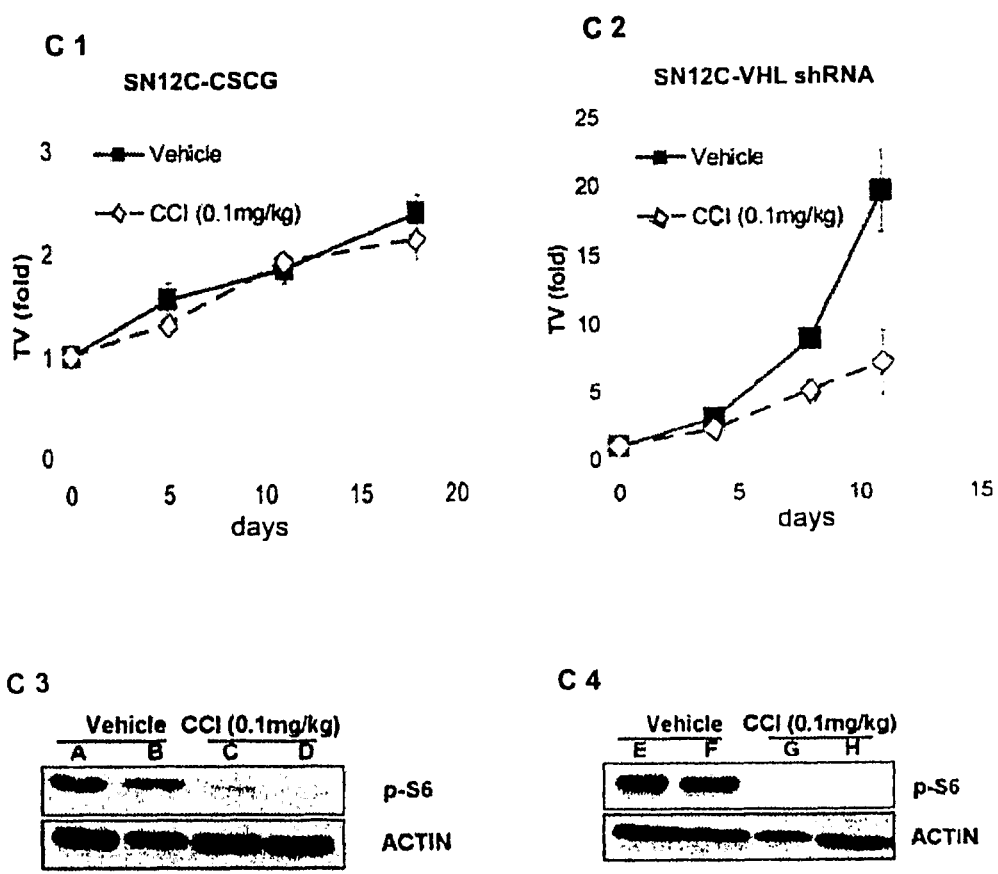

The techniques and procedures described or referenced herein are generally well understood and commonly employed using conventional methodology by those skilled in the art, such as, for example, the widely utilized molecular cloning methodologies described in Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted. Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

"Mammal" for purposes of treatment or therapy refers to any animal classified as a mammal, including humans, domestic and farm animals, and zoo, sports, or pet animals, such as dogs, horses, cats, cows, etc. Preferably, the mammal is human.

The terms "cancer", "cancerous", or "malignant" refer to or describe the physiological condition in mammals that is typically characterized by unregulated cell growth. Examples of cancer include but are not limited to astrocytoma, blastoma, carcinoma, glioblastoma, leukemia, lymphoma and sarcoma. More particular examples of such cancers include adrenal, and ophthalmologic cancers, brain cancer breast cancer, ovarian cancer, colon cancer, colotectal cancer, rectal cancer, squamous cell cancer, small-cell lung cancer, non-small cell lung cancer, Hodgkin's and non-Hodgkin's lymphoma, testicular cancer, esophageal cancer, gastrointestinal cancer, renal cancer, pancreatic cancer, glioblastoma, cervical cancer, glioma, liver cancer, bladder cancer, hepatoma, endometrial carcinoma, salivary gland carcinoma, kidney cancer, liver cancer, prostate cancer, vulval cancer, thyroid cancer, hepatic carcinoma and various types of head and neck cancer.

"Growth inhibition" when used herein refers to the growth inhibition of a cell in vitro and/or in vivo. The inhibition of cell growth can be measured by a wide variety of methods known in the art. A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Such agents further include inhibitors of cellular pathways associated with disregulated cell growth such as the PI3K/Akt pathway. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995).

"Treatment" or "therapy" refer to both therapeutic treatment and prophylactic or preventative measures. The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing tumor burden or volume, the time to disease progression (TTP) and/or determining the response rates (RR).

The term "antibody" is used in the broadest sense and specifically covers single monoclonal antibodies and antibody compositions with polyepitopic specificity (e.g. polyclonal antibodies) as well as antibody fragments so long as retain their ability to immunospecifically recognize a target polypeptide epitope.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other inmunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al. *J. Mol. Biol.*, 222:581-597 (1991), for example.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T) can also be uracil (U); this definition pertains to the differences between the chemical structures of DNA and RNA, in particular the observation that one of the four major bases in RNA is uracil (U) instead of thymidine (T).

As used herein, the term "polypeptide" means a polymer of at least about 10 amino acids. Throughout the specification, standard three letter or single letter designations for amino acids are used. In the art, this term is often used interchangeably with "protein".

Physiological Processes Pertinent to the Invention

The most common mutation in kidney cancers is loss of the Von Hippel Lindau (VHL) tumor suppressor gene, accounting for approximately 55-70% of cases (see, e.g. Gnarra et al., Urol Clin North Am 20, 207-16 (1993), Gnarra et al., Nat Genet 7, 85-90 (1994), Herman et al., Proc Natl Acad Sci USA 91, 9700-4 (1994)). VHL functions as the E3 ligase which ubiquitinates and subsequently targets Hypoxia Inducible Factor-α subunits (HIF-1, -2 and -3α), to the 26S proteosome for degradation. The HIF complex (consisting of heterodimers of HIFα subunits and HIF-1β) is a master transcription factor responsible for the activation of genes encoding for angiogenesis, glucose metabolism, pH regulation, cell proliferation, invasion and metastases (see, e.g. Seagroves et al., Cancer Cell 1, 211-3 (2002)). How inhibition of mTOR could elicit these clinical responses in a cancer where the predominant transforming event is neither a kinase mutation nor a phosphatase deficiency was unclear.

We hypothesized that loss of the VHL tumor suppressor gene plays a role in defining these clinical responses. While the frequency of VHL loss does not correspond to the known objective response rate to mTOR inhibitors, the disease stabilization rates of 50% more closely approximates VHL inactivation and the known cytostatic effects of mTOR inhibitors. The major targets of mTOR are components of the translational machinery (see, e.g. Hay et al., Genes Dev 18, 1926-45 (2004)). Growth factor RTKs recruit the PI3K/AKT pathway, initiating a signaling cascade that results in constitutive activation of mTOR, ultimately driving protein synthesis, either through cap dependent translation (i.e. through the inactivation of 4E-BP1 and subsequent activation of eIF-4e) or ribosome biogenesis (which enhances the translational efficiency of mRNA transcripts containing terminal oligopyrimidine tracts at their 5' end (5' TOP)). Significantly, HIF-α mRNA contains 5'TOP sequences sensitive to S6K.

Figure 6:
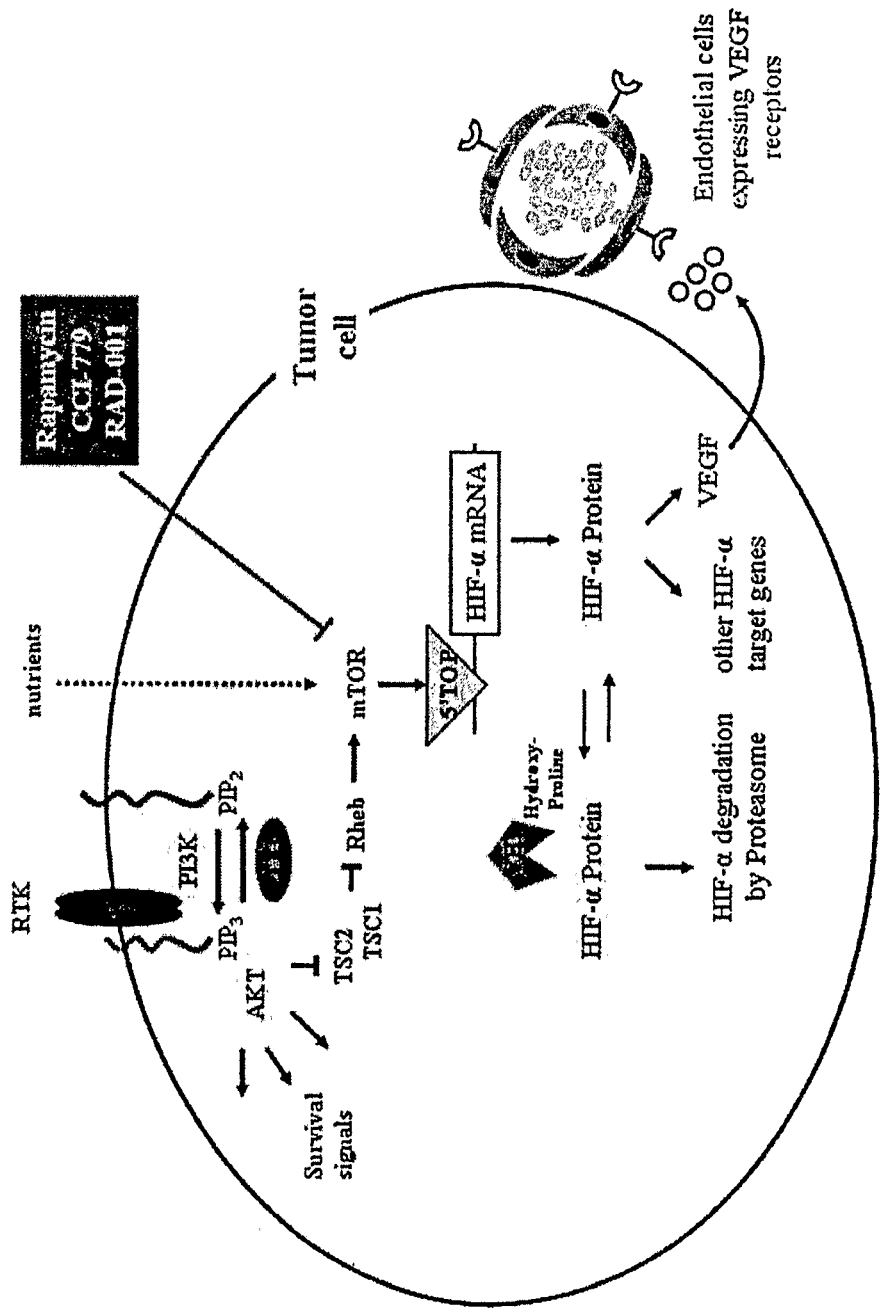
FIG. 6. mTOR regulates translation of HIF-1α and -2α in the setting of VHL loss.

VHL syndrome patients have germline mutations in one copy of the VHL gene, and the tumors that develop in these patients have mutation or deletion of the remaining allele. Somatic, biallelic VHL inactivation also occurs extremely frequently in non-hereditary cases of RCC, accounting for up to 55-70% of cases (see, e.g. Gnarra et al., Urol Clin North Am 20, 207-16 (1993), Gnarra et al., Nat Genet 7, 85-90 (1994), Herman et al., Proc Natl Acad Sci USA 91, 9700-4 (1994)). This mutation rate was closet to the 50% disease stabilization rates we were seeing in CCI-779 treated patients. VHL serves as the E3 Ligase for the HIF family of transcription factors (HIF-1α, HIF-2α and HIF-3α) (see, e.g. Ivan, et al., Curr Opin Genet Dev 11, 27-34 (2001), Kondo et al., Exp Cell Res 264, 117-25 (2001)). At least HIF-1 and -2α serve as master transcription factors responsible for the activation of genes encoding for angiogenesis, metabolism, cell proliferation and invasion/metastases. Several lines of experiments have pointed to the role of mTOR in regulation HIF-1α protein expression, most likely by increased translation of HIF-1α mRNA, which contains 5' TOP sequences, sensitive to the mTOR effector S6K (see, e.g. Laughner et al., Mol Cell Biol 21, 3995-4004 (2001)). Examination of the 5'UTR of both HIF-1α and HIF-2α reveals the presence of TOP sequences (runs of 8, 9 and 17 for HIF-1α and 8, 10, 11, 15 for HIF-2α). This is in contrast to VHL, which regulates HIF-1α and -2α post-translationally (FIG. 6). Using isogenic lines created by the stable knockdown of VHL, we see increased expression of HIF-1 and -2α protein. Treatment of these cells with CCI-779 resulted in a reduction in HIF-1 and -2α protein levels, without exerting any effect on transcription.

We hypothesized that these tumor cells have now become dependent on the excess HIF and upregulate the translational machinery (perhaps through an autocrine feedback loop involving HIF regulated growth factor genes such as TGF-α, PDGF-B, IGF-2 or VEGF (see, e.g. Harris, A. L. Nat Rev Cancer 2, 38-47 (2002)), with subsequent signaling through the PI3K pathway. We further postulate that this dependence on the pathway makes these cells more susceptible/vulnerable to mTOR inhibitors. Due to its extremely short half-life under normoxic conditions, HIF protein synthesis is likely to be particularly sensitive to changes in the rate of synthesis. The positive balance in favor of protein production and lack of degradation would ensure a constant excess of HIF under normoxic conditions. The mechanism of this was dependent on HIF translation, as it was completely reversed by the addition of prolyl hydroxylation defective mutant HIF cDNA's without the 5'TOP sequences. We also noted that these cells displayed both in vitro and in vivo sensitivity to CCI-779. The in vivo component is more easily explainable by the marked angiogenesis, which was permissive for tumor initiation and growth. The in vitro component suggests to us that these tumor cells are capable of initiating a distinct growth factor driven proliferation program. Kinetics of both components are abrogated by inhibiting mTOR. Our model system enables us to tease out the relative contributions of each of these components and explore combinatorial regimens that target these efficiently, especially in metastatic kidney cancer.

This study also for the first time, harnesses FDG PET for use in kidney cancers. FDG signal would be predicted to be higher in patients with VHL loss and thus advocates the utility of these modes of bioimaging to select the appropriate patients who will benefit most from molecularly targeted therapies. In addition, serial FDG PET Scans can be used to monitor treatment efficacy.

Out results provide new insights into mTOR inhibition and subsequently kinase dependency. Here, the activating mutation is the E3 ligase, VHL. In tumors where HIF driven gene expression is regulated by VHL (e.g. clear cell RCCs, haemangioblastomas, and subsets of phaeochromocytomas), loss of this negative regulator of the HIF complex results in its stabilization and accumulation. Recent data has shown that signaling through the PI3K/AKT/mTOR pathway favors oncogenic transformation through modulating translation (see, e.g. Rajasekhar et al., Mol Cell 12, 889-901 (2003)). The net effect, in the setting of VHL loss, is the continued translation of HIF protein, which subsequently drives the tumor, through its oncotranscriptome program. By inhibiting the translational effector, mTOR, we are then able to decrease the production of HIF and have a net protein loss despite continued stabilization.

This novel mechanism of kinase dependency, where the translation of an effector molecule determines reliance on a specific oncogenic pathway, opens the possibility of treating other cancers initiating similar programs. An obvious starting point would be to look at oncogenes translationally regulated by mTOR, e.g. Cyclin D1 (see, e.g. Schmelzle et al., Cell 103, 253-62 (2000)). Protein overexpression of this cell cycle regulator has been found in mantle cell lymphomas, as well as in breast and ovarian cancers. Targeting mTOR in subsets of these cancers that overexpress Cyclin D1 (i.e. now the biomarker) would be the impetus to individualizing molecular targeted therapies.

Figure 1D:
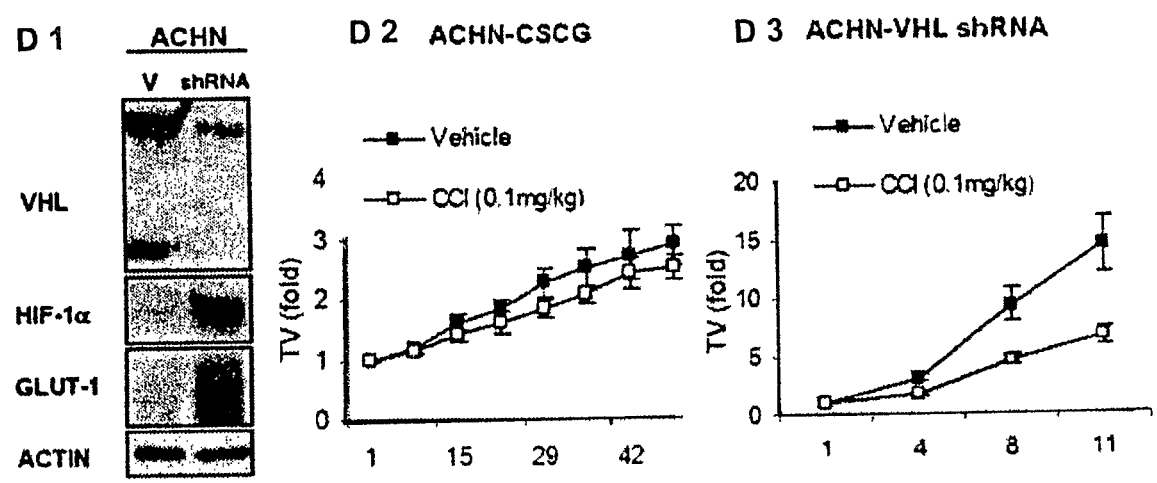
Figure 1E:
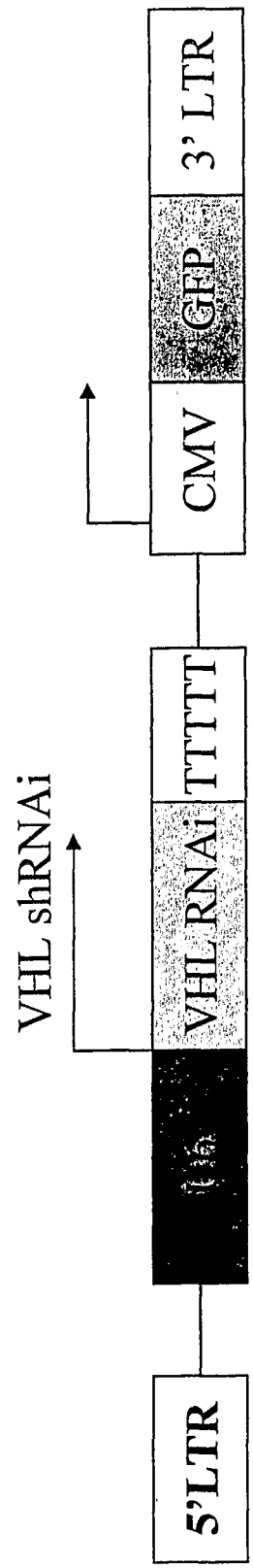
Figure 2A:
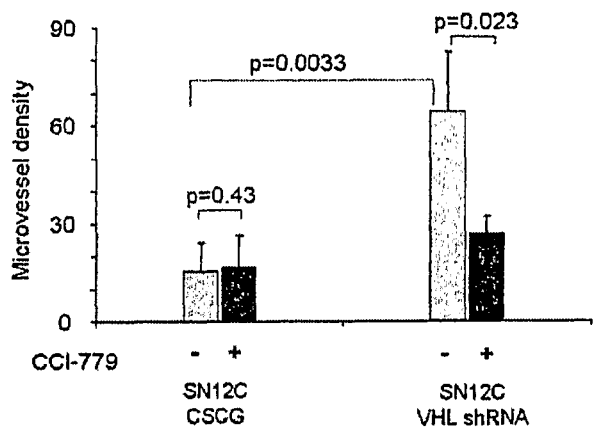
FIGS. 2A-2C. Effects of VHL knockdown on angiogenesis. (a) Microvessel density was quantified by CD-31 immunolabeling (arrows) in the xenograft tumors, and difference between CCI-779 treated (+) and vehicle (−) treated mice quantified (n=6 in each group). P<0.0033 for microvessel density counts in VHL shRNA compared to vector only (see blue bars). (b) Similar number of cells were plated and maintained in 10% serum rich media, in the presence (+) or absence (−) of 10 nM CCI-779. Thirty-six hours later, conditioned media was analyzed by anti-VEGF ELISA and cell extracts prepared for protein quantification. VEGF values were normalized to total cellular protein. Error bars equal one standard deviation (n=3). (c) Immunohistochemistry for VEGF protein was performed on paraffin embedded tumor xenografts from vehicle and CCI-779 treated mice.
Figure 2B:
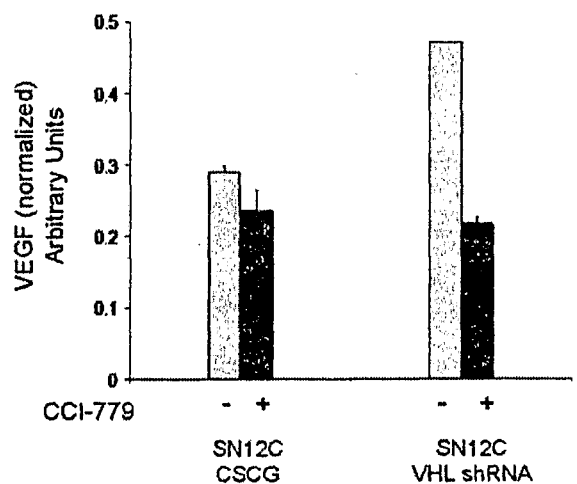
Figure 3A:
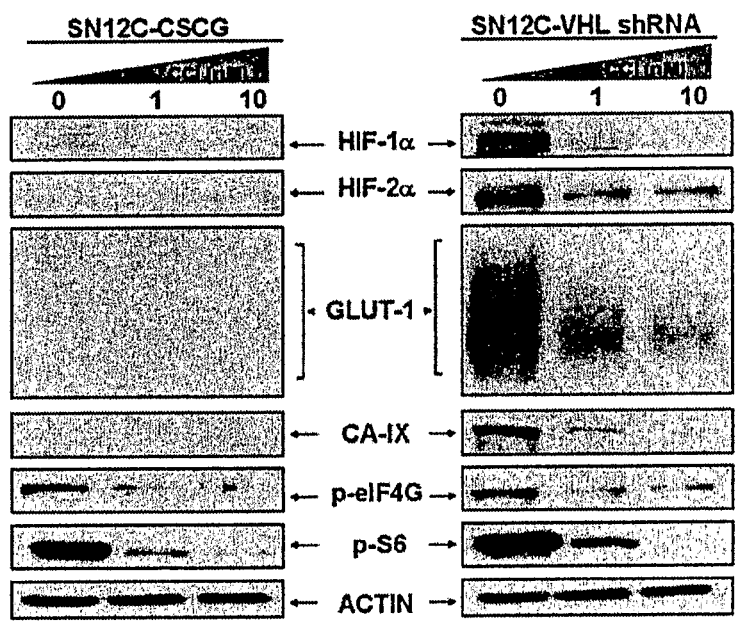
FIGS. 3A-3B. Inhibition of HIF translation by CCI-779 through 5' TOP sequences.
(a) SN12C-CSCG and SN12C-VHLshRNA cell were treated with vehicle, 1 nM or 10 nM of CCI-779 and lysed 24 hours later. Lysates were subjected to immunoblotting for HIF-1α, HIF-2α, GLUT-1, CA-IX, p-eIF4G, p-S6 Ribosomal protein. Equal protein loading was verified using anti-β-actin antibody. (b) HIF-1α expression was probed by immunoblotting in SN12C-MSCV-5'TOP-HIF-1α cDNA (left panel) and SN12C-MSCV-HIF-1α cDNA (tight panel) post 24 hours of vehicle, 1 nM or 10 nM of CCI-779.
Figure 3B:
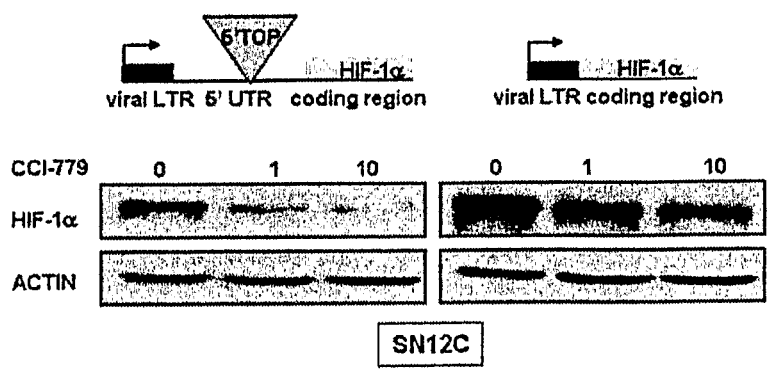

Disclosure Showing VHL Loss Determines Sensitivity to mTOR Inhibitors Through the HIF Complex
Functional Knockdown of VHL Results in HIF Stabilization To determine the molecular mechanism of CCI-779 action in kidney cancers, we utilized the NCI60 database to identify suitable cell lines. We identified two VHL Wild Type Renal Cell Carcinoma (RCC) cell lines, SN12C and ACHN (see, e.g. Scherf et al., Nat Genet 24, 236-44 (2000)). The VHL status of these cell lines have been reported (see, e.g. Maxwell et al., Nature 399, 271-5 (1999)). In addition to containing a functional VHL gene, both lines were PTEN Wild Type, thus removing any confounding variables from the known sensitivity of PTEN null cells to mTOR inhibitors. We decided to create lines with stable RNA interference to address the question of VHL status on sensitivity to CCI-779 within defined isogenic systems. Knockdown of VHL was achieved using a lentivirus vector expressing a short hairpin RNA (shRNA) against VHL, cis-linked to a green fluorescent protein (GFP) expression cassette (FIG. 1E). Stable knockdown of VHL was confirmed by Western blot and subsequent upregulation of HIF-1 and -2α was seen. We next tested the functionality of this knockdown by looking at the protein levels of transcriptional targets of HIF. Targets with canonical hypoxia response elements, which have been previously shown to be involved in tumor glycolytic, metabolic and angiogenic programs, namely glucose transporter-1 (GLUT-1), carbonic anhydrase-9 (CA-IX) and the vascular endothelial growth factor (VEGF) were assayed. Increase of these proteins by immunoblot and ELISA correlated with HIF-1 and -2α upregulation (FIG. 1A; FIG. 2B, WHITE BARS) and speaks to the efficiency of this prototypic functional knockdown of VHL.
mTOR Regulates the Translation of HIF Treatment with 1 and 10 nM of CCI-779 was sufficient to causes a decrease in HIF-1 and -2α protein levels in RCC cell lines with VHL knockdown. Simultaneous examination of the lysates for p-S6 and p-EIF4g showed a reduction in phosphorylation with CCI-779 treatment in both parental and knockdown cells. This implies inhibition of mTOR activity. The reduction in HIF-1 and -2α protein levels was closely followed by a decrease in the expression of GLUT-1, CA-IX and VEGF (FIGS. 3A, 3B).

To determine if these effects were transcriptionally regulated, we performed Real Time PCR experiments in parallel. We did not see any changes in HIF-1α transcript levels as a consequence of CCI-779 treatment. To examine the significance of the 5'TOP sequences in defining HIF-1α translation, we overexpressed HIF-1α cDNA with and without the 5' TOP sequences. Expression of the 5'TOP sequences resulted in a decrease in HIF-1α protein levels when exposed to CCI-779. This result indicates that HIF-1α translation is mTOR-dependent. Given the presence of 5'-TOP sequences in the 5' untranslated region of the HIF-2α mRNA, a similar mechanism is felt to regulate its translation.

Enhanced In Vitro and In Vivo Sensitivity of VHL shRNA RCC Cells to CCI-779 Treatment To assess the role of mTOR in proliferation mediated by VHL knockdown, we exposed the isogenic pairs of human kidney tumor cell lines to CCI-779, using the dose range elucidated from the previous experiments. Parental cells expressing the empty vector were not sensitive to CCI-779 at these doses, consistent with out hypothesis. Of note, we saw that the VHL shRNAi cells grew faster in vitro, which is in keeping with previously published reports that VHL null status results in increased growth in vitro (see, e.g. Gunaratnam et al., J Biol Chem 278, 44966-74 (2003), Datta et al., Cancer Res 61, 1768-75 (2001), Chen et al., Cancer Res 55, 4804-7 (1995)). Remarkably, the SN12C-VHL shRNAi cells showed increased sensitivity to CCI-779 in contrast to the parental cells (FIG. 1B). This suggests that the kinetics of sensitivity to mTOR inhibitors, in the setting of VHL loss, arises at least in part, due to cell autonomous mechanisms.

We next tested the in vivo activity of CCI-779 in two separate isogenic RCC xenografts. SCID mice were injected subcutaneously with SN12C-CSCG (Vector Control), SN12C-shVHL RNAi, ACHN-CSCG and ACHN-shVHL RNAi cells. Mice were assigned to treatment with 0.1 mg/kg CCI-779, when tumors reached approximately 200 mm$^3$ in size, versus vehicle control. At this dose, CCI-779 had no effect on the growth of the parental tumors. In contrast, this dose was completely blocked the growth of the VHL shRNAi tumors (FIG. 1). Similar data were seen for both cell lines. We examined the effect of CCI-779 on S6 kinase inhibition by measuring S6 levels and phosphorylation in tumors harvested on day 5 of treatment with the 0.1 mg/kg dose. In xenograft tumors from both parental and knockdown cells, there was a decrease in S6 phosphorylation, indicating effective inhibition of mTOR (FIG. 1).

Targeted Inhibition of Angiogenesis

Figure 7:
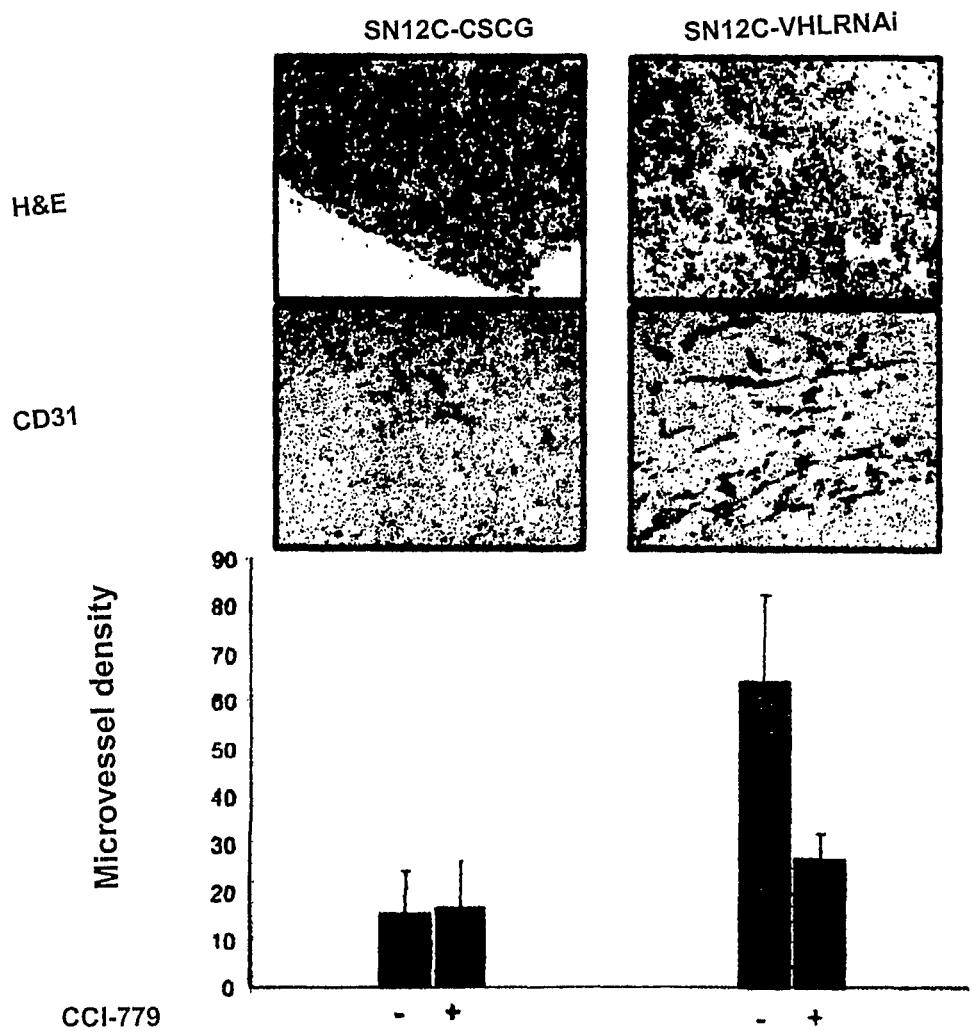
FIG. 7 The effect of angiogenesis on tumor growth (using microvessel density to score angiogenesis). VHL knockdown tumors were much mote vascular when compared to parental tumors, suggesting that angiogenic dependent factors played a part in the progression of these tumors. Treatment with CCI-779 caused an objective decrease in angiogenesis (as measured by microvessel density, (tight panel and right bar charts). VEGF immunohistochemistry performed on these tumors showed increased protein expression in the VHL knockdown xenografts, which was reduced by treatment with CCI-779.

We then examined the effect of angiogenesis on tumor growth (using microvessel density to score angiogenesis). VHL knockdown tumors were much more vascular when compared to parental tumors, suggesting that angiogenic dependent factors played a part in the progression of these tumors. Treatment with CCI-779 caused an objective decrease in angiogenesis (as measured by microvessel density, FIG. 7; RIGHT PANEL AND RIGHT BAR CHARTS). VEGF immunohistochemistry performed on these tumors showed increased protein expression in the VHL knockdown xenografts, which was reduced by treatment with CCI-779 (FIG. 7).

Targeted Inhibition of Aerobic Glycolysis

FDG PET scans that show increased basal levels of FDG in VHL K/D cells and response to CCI. See FIG. 5.

A HIF Dependent Sensitivity Phenotype

To determine if the enhanced sensitivity of the VHL knockdown cells could be explained by HIF-1α and HIF-2α translation, we overexpressed prolyl-hydroxylation defective HIF-1α (P564A) and HIF-2α (P531A) cDNA i.e. without the 5'TOP and which in addition, escapes VHL control. Stable expression of these constructs would ensure constitutive HIF expression, regardless of VHL levels. Overexpression of these mutants resulted in increased HIF-1α and HIF-2α protein levels. These mutants remained transcriptionally functional, as seen by the increased production of GLUT-1 and CA-IX (FIG. 4). Levels of these proteins were not affected by treatment with CCI-779 as the 5'TOP sequences were not present, in direct contrast to the VHL knockdown cells (FIG. 4). This occurred despite effective inhibition of mTOR activity as noted by decreased phosphorylation of S6 and e-IF4G. Next, we asked if stable overexpression of HIF-1α and HIF-2α mutants would confer resistance to the anti-proliferative effects of CCI-779. Expression of these VHL insensitive mutants resulted in a reversal of both the in vitro and in vivo sensitivity to CCI-779 (FIG. 4).

Typical Methods of the Invention

As noted above, loss of VHL results in stabilization of Hypoxia Inducible Factor complex (e.g. HIF-1α and HIF-2α, a master transcription factor responsible for the activation of genes encoding for angiogenesis, glucose metabolism, pH regulation, cell proliferation, invasion, and metastases, i.e. GLUT-1, CA-IX (CA9) and VEGF. Activation of mTOR pathway results in upregulation of S6K and inactivation of 4E-BP1, ultimately driving protein synthesis, including that of HIF-1α, and HIF-2α. This mechanism is felt to occur through S6K, which enhances the translational efficiency of mRNA transcripts containing terminal oligopyrimidine tracts at their 5' end (5' TOP). HIF-1α and HIF-2α mRNA contains 5'TOP sequences sensitive to S6K. In our preclinical data, we found that kidney tumors with loss of VHL are extremely sensitive to inhibitors of mTOR. Currently, there are no methods described in the art for detecting of the activation state of this pathway in routinely processed formalin fixed, paraffin embedded patient biopsy, and nephrectomy samples as well as measuring levels in peripheral blood mononuclear leukocytes (PBMC) and serum. A first step is to demonstrate that these antibodies can detect coordinate regulation of this pathway. We have demonstrated this. In addition, we have shown the utility of FDG-PET in detecting activation of this pathway. A second step will be to test the effectiveness of current inhibitors of the HIF pathway in these patients and to develop new inhibitors of this pathway. These reagents will therefore have immediate clinical application and relevance.

The instant disclosure shows how the loss of the VHL tumor suppressor gene plays a role in defining the clinical response to M-TOR inhibitors in kidney cancers by stabilizing the transcription regulator, Hypoxia Inducible Factor complex. For example, treatment with CCI-779 reduces HIF protein levels in these cells and we show a correlation between VHL loss and CCI-779 sensitivity in human kidney cancer cells, both in vitro and in vivo, indicating that VHL loss confers a cell autonomous and an angiogenic competitive advantage. Without being bound by a specific theory, the data provides evidence that this mechanism occurs through S6K, which enhances the translational efficiency of mRNA transcripts containing terminal oligopyrimidine tracts at their 5' end (5' TOP). As disclosed herein an understanding of this relationship between VHL and HIF can be clinically used to both select patients and monitor treatment efficacy.

Typically, the methods of the invention are used in evaluating the whether a tumor such as a kidney cancer is likely to respond (i.e. is likely to exhibit growth inhibition) when contacted with an mTOR inhibitor. In such embodiments, the status of a biomarker polypeptide that is associated with the activation of a pathway (e.g. VHL loss and/or an upregulation or stabilization of the HIF complex) is examined to determine if the pathway is disregulated in that tumor and is therefore susceptible to inhibition by a inhibitor (e.g. CCI-779 or an analog thereof) known to target that pathway. In such embodiments, the tumor is examined prior to its exposure to the inhibitor. Alternatively, the methods evaluate whether a tumor such as a kidney cancer is responsive (i.e. exhibits growth inhibition) to an mTOR inhibitor. In such embodiments, the activity of a biomarker polypeptide that is associated with the activation of a pathway (e.g. a VHL loss and/or an upregulation or stabilization of the HIF complex) is examined after the tumor is exposed to the inhibitor to determine if the biomarkers in the pathway respond to exposure to the inhibitor.

In addition, as the art that teaches that this growth related pathway is common pathway that is disregulated in a wide variety of human cancers. Consequently, artisans understand that the methods and materials disclosed herein can be universally applied to examine this pathway in all cancers in which VHL loss and/or an upregulation or stabilization of the HIF complex is observed. In this context, while the use of the disclosed methods and materials in the examination of kidney cancers represent preferred embodiments of the invention, artisans understand that these are illustrative embodiments and that these methods and materials can be applied to a wide variety of human cancers. Such cancers include but are not limited to hemangioblastomas (see, e.g. Lemeta et al., J Neuropathol Exp Neurol. 2004 October; 63(10):1072-9), Follicular thyroid tumors (see, e.g. Hunt et al., Surgery. 2003 December; 134(6):1043-7; discussion 1047-8), pancreatic cancers (see, e.g. Kim et al., Mod Pathol. 2003 November; 16(11):1086-94) and Pheochromocytomas (see, e.g. Veglio et al., Minerva Med. 2003 August; 94(4):267-71).

An illustrative embodiment of the invention is a method for identifying a mammalian tumor that is likely to respond, or is responsive to an mTOR polypeptide inhibitor (e.g. rapamycin, SD-RAD, CCI-779, RAD 001, or AP23573), the method comprising examining cells in a biological sample for a decrease in the expression of the Von Hippel Lindau (VHL) tumor suppressor gene products; and/or a stabilization or upregulation of HIF complex (comprising HIFα subunits HIF-1α, HIF-2α and HIF-3α and HIF-1β); herein a decrease in the expression of the Von Hippel Lindau (VHL) tumor suppressor gene products (e.g. VHL mRNAs or proteins); or a stabilization or upregulation of HIF complex in the cells of a control, identifies the cells in a biological sample as likely to respond or responsive to an mTOR inhibitor. Optionally, the mammalian tumor is a cancer of the kidney. A variety of methods can be used in these examinations. In one embodiment, the methods use F-18 fluorodeoxyglucose-positron emission tomography. In another embodiment, the methods use an antibody that binds that binds Von Hippel Landau (VHL) tumor suppressor gene or HIF-1α, HIF-2α, HIF-3α and HIF-1β. In yet another embodiment, the methods use a polynucleotide that hybridizes to Von Hippel Lindau (VHL) tumor suppressor gene or HIF-1α, HIF-2α, HIF-3α and HIF-1β.

As described herein, the status of VHL and/or HIF complex polypeptides and/or polynucleotides in cells of a patient suffering from or suspected of suffering from a kidney cancer may be evaluated in by a variety of methods well known in the art. The evaluation of the status of VHL and/or HIF complex provides information useful in diagnostic and prognostic protocols to assess the status of cells which may have disregulated growth. In preferred embodiments, the invention consists of methods for detecting evidence of disregulated growth in a cell such as a cell suspected of being cancerous. In these methods the status of the VHL and/or the HIF complex genes are examined by any of a number of art accepted protocols such as a genomic Southerns to evaluate gross perturbations of genomic DNA, Northern and PCR analysis to evaluate the levels VHL and/or the HIF complex mRNAs or immunological methods to examine VHL and/or the HIF complex proteins. Such protocols are used to examine the level of VHL and/or the HIF complex expression as well as the presence or absence of mutations within the VHL and/or the HIF complex mRNA or proteins. In this context, these methods are used to compare the status of VHL and/or the HIF complex in the test cell to the status of VHL and/or the HIF complex gene(s) in a corresponding normal cell or to a specific known standard, where an alteration in the status of VHL and/or the HIF complex gene(s) in the test cell relative to the normal cell provides evidence of disregulated growth within the test cell.

In specific illustrative embodiments of these methods, the status of the VHL and/or the HIF complex gene(s) is determined by a protocol selected from the group consisting of Southern hybridization, Northern hybridization, Western blotting, polymerase chain reaction and polynucleotide sequencing. In a preferred embodiment of this method, the status of VHL and/or the HIF complex gene(s) is examined by evaluating the level of mRNA transcripts within the cell. In another preferred embodiment, the cell analyzed in this method is from a biopsied tissue sample. In a specific embodiment of this method, the test cell is a human cell. In a more specific embodiment of this method, the test cell is suspected of being a tumor cell. In a highly preferred embodiment, the test cell suspected of being a tumor is selected from the group consisting of a kidney cell or another cancer observed to have VHL loss such as an adrenal cancer, a brain cancer or an ophthalmic cancer.

As discussed in detail herein, the status of VHL and/or HIF complex gene products in patient samples can be analyzed by a variety protocols that are well known in the art including F-18 fluorodeoxyglucose-positron emission tomography, immunohistochemical analysis, the variety of Northern blotting techniques including in situ hybridization, RT-PCR analysis (for example on laser capture micro-dissected samples), Western blot analysis and tissue array analysis. More particularly, the invention provides assays for the evaluation of VHL and/or HIF complex polynucleotides in a biological sample, such kidney, and other tissues, cell preparations, and the like. VHL and/or HIF polynucleotides which can be evaluated include, for example, a VHL and/or HIF gene or fragment thereof, and VHL and/or HIF mRNAs. A number of methods for amplifying and/or detecting the presence of VHL and/or HIF complex polynucleotides are well known in the art and can be employed in the practice of this aspect of the invention.

In one embodiment, a method for detecting VHL and/or HIF complex mRNAs in a biological sample comprises producing cDNA from the sample by reverse transcription using at least one primer; amplifying the cDNA so produced using an VHL and/or HIF complex polynucleotides as sense and antisense primers to amplify VHL and/or HIF complex cDNAs therein; and detecting the presence of the amplified VHL and/or HIF complex cDNAs. Optionally, the sequence of the amplified VHL and/or HIF complex cDNAs can be determined.

In another embodiment, a method of detecting a VHL and/or HIF complex genes in a biological sample comprises first isolating genomic DNA from the sample; amplifying the isolated genomic DNA using VHL and/or HIF polynucleotides as sense and antisense primers; and detecting the presence of the amplified VHL and/or HIF genes. Any number of appropriate sense and antisense probe combinations can be designed from the nucleotide sequences of VHL and/or HIF and used for this purpose.

The invention also provides assays for detecting the presence of an VHL and/or HIF complex proteins in a tissue or other biological sample such as kidney and other tissues, and the like. Methods for detecting a VHL and/or HIF complex proteins are also well known and include, for example, immunoprecipitation, immunohistochemical analysis, Western blot analysis, molecular binding assays, ELISA, ELIFA and the like. For example, a method of detecting the presence of a VHL and/or HIF protein in a biological sample comprises first contacting the sample with a VHL and/or HIF complex antibody, a VHL and/or HIF-reactive fragment thereof, or a recombinant protein containing an antigen binding region of a VHL and/or HIF complex antibody; and then detecting the binding of VHL and/or HIF-related protein in the sample.

One illustrative embodiment of the invention is a method for identifying a mammalian tumor cell (e.g. a kidney cancer cell) that is likely to respond, or is responsive to an mTOR polypeptide inhibitor, the method comprising examining the mammalian tumor cell for an at least 50%, 60%, 70%, 80%, 90% or 95% decrease in the expression of the Von Hippel Lindau (VHL) tumor suppressor protein in the mammalian tumor cell as compared to a control cell of the same cellular lineage as the mammalian tumor cell; wherein an at least 50%, 60%, 70%, 80%, 90% or 95% decrease in the expression (i.e. a relative decrease in observed VHL protein levels) of the Von Hippel Lindau (VHL) tumor suppressor protein identifies the mammalian tumor cell as likely to respond or responsive to an mTOR polypeptide inhibitor. A variety of mTOR inhibitors are known in the art (see, e.g. Mita et al., Cancer Biol Ther. 2003 July-August; 2(4 Suppl 1):S169-77; Rowinsky Curr Opin Oncol. 2004 November; 16(6):564-75; Kristof et al., J Pharmacol Exp Ther. 2005 September; 314 (3):1134-43. Epub 2005 May 27; Giles et al., Curr Mol Med. 2005 November; 5(7):653-61). Typically, the mTOR polypeptide inhibitor is rapamycin, SDZ-RAD, CCI-779, RAD 001, AP23573 or the like. A variety of methods for examining levels (e.g. to observe a decrease in the expression) of the Von Hippel Lindau (VHL) tumor suppressor protein are known in the art (see, e.g. Palayoor et al., Clin Cancer Res. 2004 Jun. 15; 10(12 Pt 1):4158-64; Na et al., J Urol. 2003 August; 170(2 Pt 1):588-92; Le et al., Clin Cancer Res. 2003 January; 9(1):59-67). As disclosed herein, the methods can be direct (i.e. by looking at the protein directly), or indirect (i.e. by looking at a factor that can be correlated to the levels of VHL protein expression). In some embodiments of the invention for example, the expression of Von Hippel Lindau (VHL) tumor suppressor protein (SEQ ID NO: 1) is examined using an antibody that binds the Hippel Lindau (VHL) tumor suppressor protein. In addition, because Von Hippel Lindau (VHL) tumor suppressor protein levels are observed to be correlated with Von Hippel Lindau (VHL) tumor suppressor mRNA levels (i.e the mRNA that encodes this protein), the expression VHL protein can therefore be examined by a method comprising observing an at least 50%, 60%, 70%, 80%, 90% or 95% decrease in the expression of mRNA encoding the Von Hippel Lindau (VHL) tumor suppressor protein (SEQ ID NO: 1). In specific methods, VHL mRNA expression is examined using a polynucleotide that hybridizes to mRNA encoding the Von Hippel Lindau (VHL) tumor suppressor protein (SEQ ID NO: 1), for example a polymerase chain reaction (PCR) method or a Northern blot method. In yet another embodiment of the invention, the presence and/or levels of the Von Hippel Lindau (VHL) tumor suppressor protein are examined by a method comprising using F-18 fluorodeoxyglucose-positron emission tomography. In yet another embodiment of the invention, the presence and/or levels of the Von Hippel Lindau (VHL) tumor suppressor protein are examined by observing a decrease in the expression of the Von Hippel Lindau (VHL) tumor suppressor protein is examined by a method comprising observing an at least 10%, 20%, 30%, 40% or 50% increase in the level of HIF-1α (SEQ ID NO: 2) or HIF-2α (SEQ ID NO: 3) polypeptide in the mammalian tumor cell as compared to a control cell of the same cellular lineage as the mammalian tumor cell.

Yet another embodiment of the invention is a method for identifying a mammalian tumor cell (e.g. a kidney cell) that is likely to respond, or is responsive to an mTOR polypeptide inhibitor, the method comprising examining the mammalian tumor cell for expression of a Von Hippel Lindau (VHL) tumor suppressor protein (SEQ ID NO: 1) having a deletion, substitution or insertion mutation as can be observed by comparing the VHL polypeptide sequence shown in SEQ ID NO: 1 to that obtained from the tumor cell; wherein a deletion, substitution or insertion mutation in the Von Hippel Lindau (VHL) tumor suppressor protein identifies the mammalian tumor cell as likely to respond or responsive to an mTOR inhibitor. Typical methodologies of this embodiment use a polynucleotide that hybridizes to mRNA encoding the Von Hippel Lindau (VHL) tumor suppressor protein (SEQ ID NO: 1), for example in a Northern blot and/or polymerase chain reaction (PCR) method. Alternatively a deletion, substitution or insertion mutation in the Von Hippel Lindau (VHL) tumor suppressor protein (SEQ ID NO: 1) is examined by a method comprising observing an at least 10%, 20%, 30%, 40% or 50% increase in the level of HIF-1α (SEQ ID NO: 2) or HIF-2α (SEQ ID NO: 3) polypeptide in the mammalian tumor cell as compared to a control cell of the same cellular lineage as the mammalian tumor cell.

Yet another embodiment of the invention is a method of monitoring the efficacy of an mTOR polypeptide inhibitor in the treatment of a mammalian tumor having a decrease in the expression of the Von Hippel Lindau (VHL) tumor suppressor protein (SEQ ID NO: 1), the method comprising examining cells in a biological sample for an at least 10%, 20%, 30%, 40% or 50% decrease in HIF-1α (SEQ ID NO: 2) and/or HIF-2α (SEQ ID NO: 3) polypeptide levels in a test cell from the mammalian tumor that has been exposed to the mTOR polypeptide inhibitor as compared to a cell from the mammalian tumor that has not been exposed to the mTOR polypeptide inhibitor; wherein such a decrease in HIF-1α (SEQ ID NO: 2) and/or HIF-2α (SEQ ID NO: 3) polypeptide levels in the test cell provides evidence that the mTOR polypeptide inhibitor is efficacious in the treatment of the mammalian tumor. Optionally, the method comprises using F-18 fluorodeoxyglucose-positron emission tomography or uses an antibody that binds a HIF-1α (SEQ ID NO: 2) or HIF-2α (SEQ ID NO: 3) polypeptide.

Typically the assays of the invention include immunohistochemical techniques. Immunohistochemical techniques as used herein encompasses the use of reagents detecting cell specific markets, such reagents include, for example antibodies. Antibodies, including monoclonal antibodies, polyclonal antibodies and fragments thereof, are often used to identify proteins or polypeptides of interest in a sample. A number of techniques are utilized to label objects of interest according to immunohistochemical techniques. Such techniques are discussed in Current Protocols in Molecular Biology, Unit 14 et seq., eds. Ausubel, et al., John Wiley & Sons, 1995, the disclosure of which is incorporated herein by reference. Typical protocols include staining a paraffin embedded tissue section prepared according to a conventional procedure (see, e.g. U.S. Pat. No. 6,631,203).

Significantly, the disclosed methods for examining these biomarkers are useful with a wide variety of tissue samples including formalin fixed, paraffin embedded biopsy samples. As disclosed herein, these markets can be examined using a panel of antibodies such as phospho-specific antibodies. In these methods, a mammalian cell such as a cell derived from a formalin fixed, paraffin embedded biopsy sample can be examined for evidence of pathway activation by examining a tissue sample containing this cell for the presence of the various target molecules disclosed herein. Certain embodiments of the invention identify and/or assess a therapeutic agent that may be used to treat the kidney cancer such as rapamycin or an analogue thereof.

Articles of Manufacture of the Invention

Embodiments of the invention also include articles of manufacture and/or kits designed to facilitate the methods of the invention. Typically such kits include instructions for using the elements therein according to the methods of the present invention. Such kits can comprise a carrier means being compartmentalized to receive in close confinement one or more container means such as vials, tubes, and the like, each of the container means comprising one of the separate elements to be used in the method. For example, one of the container means can comprise one or more of the antibodies disclosed herein (an VHL and/or HIF antibody) that is or can be detectably labeled with a marker. For kits utilizes immunological methods (e.g. immunohistochemistry and Western blotting) to detect the target proteins, the kit can also have containers containing buffers for these methods and/or containers comprising antibodies labelled with a reporter-means, such as a chromophore or radioactive molecule.

In a typical embodiment of the invention, an article of manufacture containing materials useful for the examination of the disorders described above is provided. The article of manufacture comprises a container and a label. Suitable containers include, for example, bottles, vials, syringes, and test tubes. The containers may be formed from a variety of materials such as glass or plastic. The container can hold a composition (e.g. an polynucleotide probe and/or antibody composition) which is effective for examining mammalian cells (e.g. kidney cancer cells). The label on, or associated with, the container indicates that the composition is used for examining cellular polypeptides. The article of manufacture may further comprise a second container comprising a buffer, such as phosphate-buffered saline, Ringer's solution and dextrose solution. It may further include other materials desirable from a commercial and user standpoint, including other buffers, diluents, filters, needles, syringes, and package inserts with instructions for use.

Throughout this application, various publications are referenced. The disclosures of these publications are hereby incorporated by reference herein in their entireties.

EXAMPLES

The Examples below provide illustrative methods and materials that can be used in the practice of the invention.

Example 1

Illustrative Methods and Materials for Practicing Embodiments of the Invention

DNA Constructs and PCR Primers.

The pCSUVCG (U6-shRNA-VHL-CMV-GFP) was constructed by ligating the BamHI/EcoRI digests of pCSCG and the U6-shRNA-VHL PCR product. The U6-shRNA-VHL PCR was performed using a hU6-containing plasmid at an annealing temperature of 60° C. with the primers 5'-xyz-3' and 5'-pqr-3'. The prolyl hydroxylation defective mutants of p-Babe-puro-HA-HIF-1α (P564A) and HIF-2α (P405A; P531A) were a generous gift of Dr. W. G. Kaelin (see, e.g. Aprelikova et al., J Cell Biochem 92, 491-501 (2004), Kondo et al., Cancer Cell 1, 237-46 (2002), Kondo et al., PLoS Biol 1, E83 (2003)).

Immunoblot Analysis and VEGF ELISA.

Cells and xenograft tumors were lysed in ECB lysis buffer (see, e.g. Kondo et al., Cancer Cell 1, 237-46 (2002)) or high-detergent buffer (2% SDS), (see, e.g. Chen et al., Nat Med 10, 33-9 (2004)), respectively, supplemented with complete protease and phosphatase inhibitor cocktails (Calbiochem). Protein extracts were resolved by SDS-PAGE and transferred to nitrocellulose membranes. After blocking in Tris-buffered saline (TBS) with 5% non-fat milk, the membranes were probed with following: anti-VHL mouse monoclonal antibody (1:400, Oncogene Research Sciences), anti-HIF1α mouse monoclonal antibody (1:250, BD Pharmingen), anti-HIF-2α mouse monoclonal antibody (1:500, Novus Biologicals), anti-GLUT-1 rabbit polyclonal antibody (1:1000, Alpha Diagnostic), anti-CA-IX rabbit polyclonal antibody (1:500, Novus Biologicals), anti-phospho-eIF4G-S1108 rabbit polyclonal antibody (1:1000, Cell Signaling), anti-phospho-S6 Ribosomal protein S235/236 rabbit polyclonal antibody (1:1000, Cell Signaling) or anti-β-actin mouse monoclonal antibody (1:5000, Sigma), diluted in TBS with 4% BSA. Bound antibody was detected using enhanced chemiluminescence (ECL, Amersham). For VEGF ELISA quantification, cells were plated in 6 well plates ($1\times10^5$ per well). Experiments were performed in triplicate. Once the cells attached, the media was changed and either 10 nM of CCI-779 or vehicle (100% ethanol) was added. Thirty-six hours later, VEGF ELISA (R&D Systems) was performed according to the manufacturer's instructions, using a Fisher Plate reader. For normalization, the VEGF protein levels were divided by the intracellular protein concentrations within each sample In Vitro and In Vivo Growth Experiments.

SN12C and ACHN (NCI60, DTP) were maintained in Dulbecco's modified Eagle's Medium (DMEM) supplemented with 10% FBS. SN12C-CSCG, ACHN-CSCG, SN12C-CSCG-VHLshRNAi and ACHN-CSCG-VHLshRNAi were derived by infecting cells with the pCSCG or pCSUVCG lentivirus respectively, without selection (>90% infection). Retroviruses containing the HIF1 and HIF-2 mutants (i.e. p-Babe-puro-HA-HIF-1α (P564A) and HIF-2α (P405A; P531A)) or the backbone vector were transfected into Phoenix packaging cell line using Lipofectamine 2000 (Invitrogen) according to the manufacturer's instruction. Tissue culture supernatant was harvested 48 hours later, passed through a 0.45μ filter and added to the SN12C-CSCG-VHLshRNAi cells in the presence of 4 ug/ml polybrene. Infected cells were selected by growth in the presence of puromycin (1.5 ug/ml).

For in vitro experiments, cells ($5\times10^4$) were plated and treated with 1 and 10 nM CCI-779 (kind gift of J. Gibbons, Wyeth) or vehicle (ethanol). On day 5-post treatment, cells were trypsinized, resuspended in DMEM with 10% FBS and counted using the VI CELL counter (Beckman Coulter), according to the manufacturer's instructions. Cell counts were done in triplicate and repeated on at least 3 independent occasions. In vivo tumorigenicity was measured by injection of $5\times10^5$ SN12C-CSCG, ACHN-CSCG, SN12C-CSCG-VHLshRNAi, ACHN-CSCG-VHLshRNAi, SN12C-CSCG-VHLshRNAi-pBABE, SN12C-CSCG-VHLshRNAi-pBABE-HA-HIF-2α (P405A; P531A) cells in 100 μl of Matrigel (Collaborative Biomedical) subcutaneously into the flanks of SCID mice. Tumor size were measured weekly in three dimensions using calipers as described (Klein, K. A. et al. Nat Med 3, 402-8 (1997)). When tumors reached 200 mm³, all tumors received 0.1 mg/kg/daily of CCI-779 or vehicle. All mouse experiments were performed in compliance with the guidelines of the Animal Research Committee of the University of California at Los Angeles.

Immunohistochemistry.

Xenograft tumor samples were fixed in 10% buffered formalin and embedded in paraffin. Thin sections (4 μm) were stained with hematoxylin and eosin according to standard protocols. Detection of CD-31 (XYZ, 1:500, Santa Cruz), anti-phospho-S6 Ribosomal protein S235/236 rabbit polyclonal antibody (XYZ, 1:1000, Cell Signaling) and anti-VEGF rabbit polyclonal antibody (XYZ, 1:1000, Santa Cruz) was by standard avidin-biotin immunoperoxidase methods, with diaminobenzidine used as the chromogen and hematoxylin as the counter stain. Microvessel density was quantified by as described previously (Weidner, N. et al. J Natl Cancer Inst 84, 1875-87 (1992)). Briefly, microvessel density was determined by light microscopy in areas of the xenograft tumor containing highest numbers of capillaries and small venules (microvessels) per area (i.e. neovascular "hotspots") by scanning the tumor sections at low power (40× and 100×). Any endothelial cell or endothelial cell cluster positive for CD-31 and clearly separate from an adjacent cluster was considered to be a single, countable microvessel and results were expressed as the highest number of microvessels identified within any single 200× field.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Example 2

Illustrative Methods and Materials for Practicing Embodiments of the Invention mTOR inhibitors have shown sporadic activity in cancer trials, leading to confusion about the appropriate clinical setting for their use. Here we show that loss of the Von Hippel-Lindau (VHL) tumor suppressor gene sensitizes kidney cancer cells to the mTOR inhibitor CCI-779 in vitro and in mouse models. Growth arrest caused by CCI-779 correlates with a block in translation of Hypoxia Inducible Factor (HIF) mRNA, and is rescued by expression of a VHL-resistant HIF cDNA lacking the 5' untranslated region that confers mTOR regulation. VHL-deficient tumors show increased uptake of the positron emission tomography (PET) tracer fluorodeoxyglucose (FDG) in a mTOR-dependent manner. Out findings provide preclinical rationale for prospective, biomarker-driven clinical studies of mTOR inhibitors in kidney cancer and suggest that FDG-PET scans may have utility as a pharmacodynamic market in this setting.

The mTOR (mammalian Target of Rapamycin) kinase inhibitor CCI-779 induces objective responses in about 10% and disease stabilization in about 50% of patients with metastatic renal carcinoma (see, e.g. Atkins, M. B. et al. J Clin Oncol 22, 909-18 (2004)). This finding of selective activity in a subset of patients raises the possibility that responders share a common molecular phenotype that renders these tumors mTOR-dependent for growth and/or survival. A similar phenomenon with EGFR inhibitors in lung has been resolved with the recent discovery that EGFR kinase domain mutations are associated with clinical responses (see, e.g. Paez, J. G. et al., Science 304 (5676):1497-500 (2004), Lynch, T. J. et al. N Engl J Med 350, 2129-39 (2004), and Pao, W. et al. Proc Natl Acad Sci USA 101, 13306-11 (2004)). The most common molecular abnormality in renal cell carcinoma is VHL loss, which is found in about 50-70% of sporadic cases (see, e.g. Kim et al., J Clin Oncol 22, 4991-5004 (2004)). VHL encodes an E3 ligase that promotes the ubiquitination of the α-subunits of the hypoxia inducible transcription factors HIF-1, -2 and -3, leading to their degradation by the proteosome. Consequently, renal carcinomas with VHL mutations have high steady state levels of HIF protein expression. Functional studies demonstrate that HIF is sufficient for transformation caused by VHL loss, thereby establishing HIF as the primary oncogenic driver in these cancers (see, e.g. Seagroves et al., Cancer Cell 1, 237-46 (2002); Kondo, K et al., Cancer Cell 1, 237-46 (2002); and Maranchie, J. K. et al. Cancer Cell 1, 247-55 (2002)).

Notably, HIF protein expression is mTOR-dependent in certain cellular contexts (see, e.g. Hudson, C. C. et al. Mol Cell Biol 22, 7004-7014 (2002), Zhong, H. et al. Cancer Res 60, 1541-5 (2000), and Semenza, G. L. Nat Rev Cancer 3, 721-32 (2003)). Most relevant to renal cell carcinoma is the fact that the 5' untranslated regions of both HIF1α and HIF2α mRNAs contain 5' terminal oligopolypyrimidine (TOP) tracts that can regulate translation in response to S6 kinase activation (see, e.g. Laughner et al., Mol Cell Biol 21, 3995-4004 (2001)). Translation of mRNAs beating 5'-TOP sequences is mTOR-dependent because mTOR regulates a kinase cascade, involving S6 kinase and its substrate S6 ribosomal protein, which is required for efficient translation of these messages. This connection between HIF translation and mTOR raised the possibility that the clinical activity of mTOR inhibitors in a subset of renal cell carcinoma may be explained, in part, by VHL loss.

We evaluated this possibility by constructing isogenic pairs of human renal carcinoma cell lines, differing only in VHL expression levels, using stable RNA knockdown by lentiviral transfer of VHL-specific shRNA. In addition to having wild-type VHL, we chose two independent parental lines (SN12C and ACHN) expressing wild-type PTEN to remove any confounding effect of PTEN loss, which is known to sensitize cells to mTOR inhibition through activation of AKT (see, e.g. Neshat, M. S. et al. Proc Natl Acad Sci USA 98, 10314-9 (2001), Podsypanina, K. et al. Proc Natl Acad Sci USA 98, 10320-5 (2001), and Houghton et al., Curr Top Microbiol Immunol 279, 339-59 (2004)). As expected, VHL protein levels were reduced and HIF-1 and -2α protein levels were increased in cells stably expressing the knockdown constructs (FIG. 1A), whereas a vector only control had no effect. Similarly, a shRNA targeting the Androgen Receptor elicited no effect. In addition, protein levels of the HIF target genes, glucose transporter-1 (GLUT-1), carbonic anhydrase-9 (CA-IX) and VEGF, were all increased in VHL knockdown cells (FIGS. 1A AND 2B) (see, e.g. Houghton et al., Curr Top Microbiol Immunol 279, 339-59 (2004); and Chen, F. et al. Cancer Res 55, 4804-7 (1995)). We also noted that VHL shRNA cells proliferated mote rapidly than their isogenic parental counterparts, in keeping with previous reports that VHL addback results in suppressed growth (FIG. 1B) (see, e.g. Houghton et al., Curr Top Microbiol Immunol 279, 339-59 (2004).

To assess the role of mTOR in proliferation mediated by VHL knockdown, we exposed both isogenic human kidney tumor cell line pairs to the mTOR inhibitor CCI-779. The growth of parental cells expressing the empty vector SN12C-

Figure 2C:
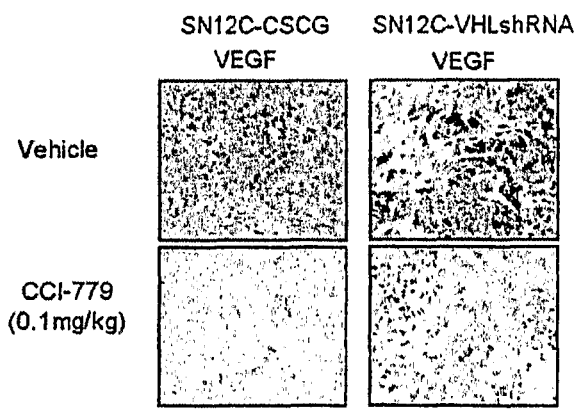

CSCG (and ACHN-CSCG) were not affected by 10 nM CCI-779, whereas growth of SN12C-VHL shRNA cells (and ACHN-VHL shRNA) was reduced by 70 percent in a dose-dependent fashion. Similar results were obtained when the isogenic lines were grown as subcutaneous xenografts in SCID mice (FIG. 1C, D). Of note, CCI-779 blocked mTOR activity in parental and VHL knockdown xenografts, as measured by a decrease in S6 phosphorylation In addition to cell autonomous effects, mTOR inhibitors can have direct anti-angiogenic activity based on the fact that endothelial cell growth is mTOR-dependent in certain settings (see, e.g. Guba, M. et al. Nat Med 8, 128-35 (2002)). Since angiogenesis is a central histologic feature of renal carcinoma, mTOR inhibitors could also impair tumor growth through effects on tumor vasculature. Indeed, xenografts from VHL knockdown cell lines were mote vascular when compared to parental tumors, as measured by CD-31 immunohistochemical staining (p<0.0033), and treatment with CCI-779 resulted in greater than 50 percent decrease in microvessel density (FIG. 2A). However, since the pro-angiogenic gene VEGF is a HIF target, the antiangiogenic properties of CCI-779 in this setting might also be a consequence of direct effects of the drug on tumor cells. Indeed, secreted VEGF levels were increased in VHL knockdown cells and reduced 2 fold by CCI-779 treatment in vitro (FIG. 2B). Xenograft tumors from VHL knockdown cells also expressed elevated levels of VEGF protein that was reversed by CCI-779 therapy (FIG. 2C).

Collectively, these experiments establish that VHL loss sensitizes renal carcinoma cells to growth inhibition by mTOR inhibitors. Furthermore, this sensitization is likely to occur primarily through direct action of the drug on tumor cells, since growth inhibition was observed in vitro and in vivo. This conclusion is consistent with the known connection between 5' TOP-dependent HIF translation and mTOR, and leads to several predictions. First, CCI-779 treatment should lower HIF-1-2α protein levels in VHL knockdown cells. Second, this effect should be dependent on the 5' TOP sequences in the untranslated region of the HIF-1, -2α mRNAs. Third, the growth inhibitory effects of CCI-779 should be rescued by expression of a HIF cDNA lacking the 5'TOP sequences and resistant to degradation by VHL.

To address the first question, we measured HIF protein levels in VHL knockdown cells after exposure to CCI-779. Expression of both HIF-1☐ and -2☐ was dramatically reduced within twenty-four hours. In addition, expression of the HIF target genes GLUT-1, CA-IX and VEGF was similarly reduced. These changes correlated precisely with inhibition of mTOR, as measured by reduced phosphorylation of downstream substrates eIF4G and S6 (FIG. 3A). Notably, CCI-779 treatment had no effect of HIF1☐ mRNA levels consistent with the hypothesis that the decreased protein levels are caused by a block in translation. This hypothesis is also supported by studies using hetetologously expressed HIF-1α in which the natural 5'TOP sequence of the untranslated mRNA was either retained or deleted from the HIF-1α cDNA expression construct. Similar to the effects seen on endogenous HIF in VHL knockdown cells, CCI-779 treatment caused a reduction in HIF-1α protein levels in VHL wild-type cells transfected with the cDNA that retained the 5' TOP sequences. In contrast, HIF-1α levels were largely unaffected by CCI-779 treatment when the 5'TOP sequence was removed (FIG. 3B).

Figure 4C:
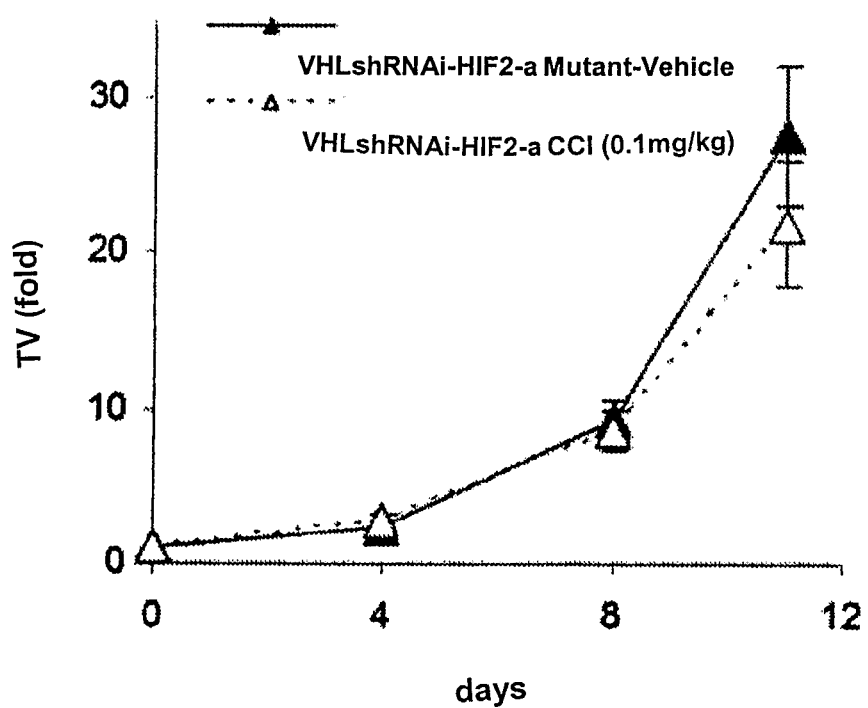

These experiments established that the growth inhibitory effects of CCI-779 on VHL deficient renal carcinoma cell lines are correlated with reduced translation of HIF protein. Prior work has demonstrated that rescue of VHL-mediated tumor suppression is conferred by HIF mutants resistant to VHL-mediated degradation. To provide functional evidence that reduced HIF levels are responsible for decreased growth in CCI-779 treated cells, we transduced SN12C VHL knockdown cell line with similar HIF-1α or HIF-2α mutant cDNAs lacking the 5' TOP sequences (P564A for HIF-1α; P351A for HIF-2α) (see, e.g. Rondo, K et al., Cancer Cell 1, 237-46 (2002); Aprelikova, O. et al. J Cell Biochem 92, 491-501 (2004)). As expected, both HIF mutants as well as downstream target genes were stably expressed in the presence or absence of CCI-779, despite clear biochemical evidence of mTOR inhibition as measured by eIF4E and S6 phosphorylation (FIG. 4A). Remarkably, expression of either mutant completely rescued VHL knockdown cells from the growth inhibitory effects of CCI-779 treatment in vitro (FIG. 4B) and in xenograft experiments (FIG. 4c). These experiments establish that the antiptoliferative activity of mTOR inhibitors in VHL null kidney cancer cells is mediated through its effect of HIF translation.

These results have important implications for ongoing clinical trials of CCI-779 in renal carcinoma and argue that VHL status could serve as a biomarker for patient selection. VHL data was not collected from the completed phase II studies in renal cancer, but one can compare the response rates in these trials with the expected frequency of VHL mutation in analogous patients. Paradoxically, the objective response rate (~10 percent) is significantly lower than the anticipated VHL mutation rate (~50 percent). However, these trials reported very high rates of stable disease (~50 percent). Not only does this number match the expected VHL mutation rate, but also stable disease may be the predicted clinical outcome of mTOR inhibition, since growth arrest (not tumor regression) was observed in our preclinical models. Alternatively, additional molecular lesions such as Bcl-2 expression could mitigate the response to mTOR inhibition (see, e.g. Majumder, P. K. et al. Nat Med (2004)). In either case, it will be important to correlate VHL status with clinical response in future trials, to determine if the preclinical association observed here might guide future patient selection.

Figures 5A, 5B:
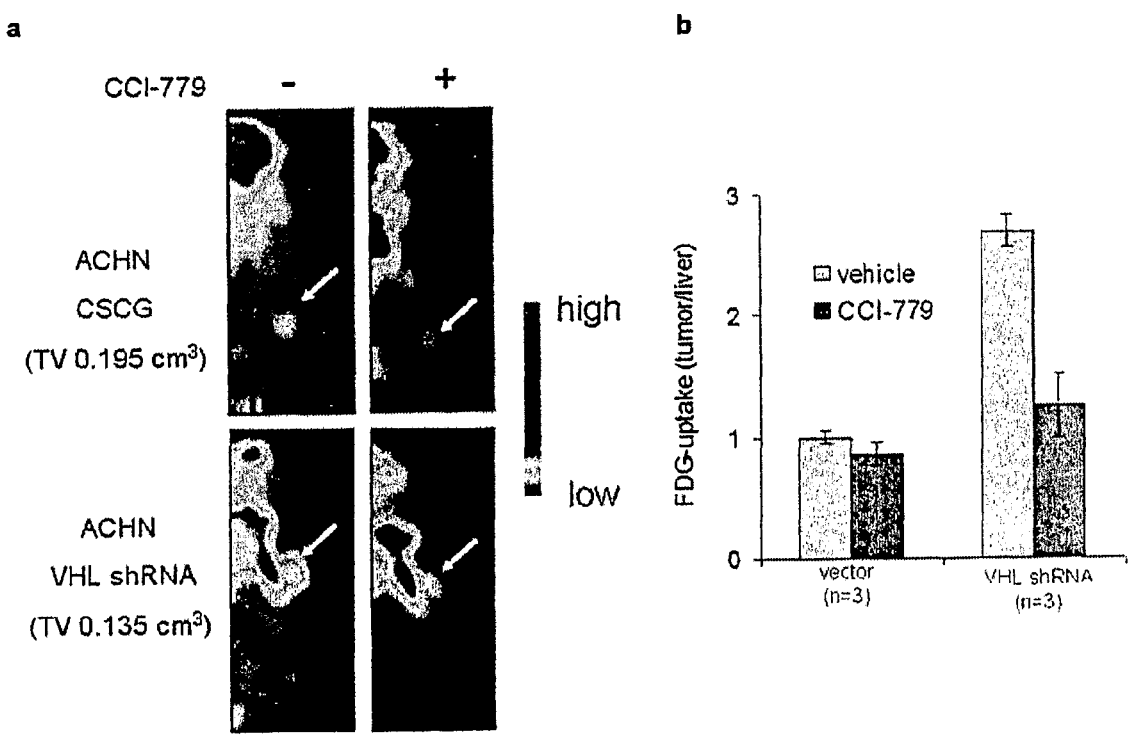
FIGS. 5A-5B. MicroPET imaging shows VHL and mTOR dependent glucose uptake. (a) Representative images of two SCID-mice bearing isogenic ACHN-xenograft tumors on the right flank before and after two doses of CCI-799 (0.1 mg/kg). Arrows indicate the location of subcutaneous xenograft tumors (innate increased signal intensity due to abdominal brown fat and glial tissue are observed in the thorax and skull of the mice). (b) Quantification of FDG uptake (+/−SEM) in SCID-mice bearing either ACHN-vector or ACHN-CSCG VHL shRNA subcutaneous xenografts. FDG-tumor uptake was normalized to hepatic FDG-uptake for each mouse. n=3 per group and experiments were repeated twice with identical results. Similar results were seen in SN12C-CSCG and SN12C-CSCG VHL shRNA xenografts.

In addition to a tissue market of VHL status, it would be extremely useful to have a non-invasive tool for monitoring VHL status and response to mTOR inhibition. Interestingly, a transcriptional signature of HIF activation, recently identified in an AKT-driven prostate cancer model, includes a number of genes in the glycolytic pathway (see, e.g. Majumder, P. K. et al. Nat Med (2004)). In addition, we noted increased expression of the HIF target gene Glut1 in our VHL knockdown cells (FIG. 1A). These findings raise the possibility that HIF-driven tumors might accumulate fluorodeoxyglucose (FDG), the widely used clinical tracer for positron emission tomography. Therefore, we compared the uptake of (see, e.g. Kaelin et al., Trends Genet 14, 423-6 (1998)) F-FDG in both of VHL knockdown xenograft models relative to parental cells. In three independent experiments, VHL knockdown tumors in both models grown as subcutaneous flank masses reproducibly showed at least a 2-fold increase in FDG uptake that was reduced to baseline within 24 hours with CCI-779 (FIG. 5). Of note, clinical PET studies in kidney cancer patients indicate that a significant proportion (~50-70%) of these tumors are FDG avid (see, e.g. Hain et al., BJU Int 92, 159-64 (2003). These results raise the possibility that FDG-PET scanning could be used to non-invasively document mTOR inhibition in renal carcinoma patients prior to and shortly after initiation of mTOR inhibitor therapy, analogous to the use of this scan in gastrointestinal stromal tumor (GIST) patients treated with imatinib (see, e.g. Joensuu, H.

Med Klin (Munich) 97 Suppl 1, 28-30 (2002), and Gayed, I. et al. J Nucl Med 45, 17-21 (2004)).

Similar to CCI-779, clinical activity has been reported in subsets of renal carcinoma using any one of several anti-angiogenesis agents that target VEGF (Bevacizumab) or its receptor VEGFR (SU11248, Bay 43-9006) (see, e.g. Ferrara et al., Nat Rev Drug Discov 3, 391-400 (2004)). Although mTOR inhibitors also have anti-angiogenic properties (see, e.g. Guba, M. et al. Nat Med 8, 128-35 (2002)), our results showing that HIF rescues growth suppression caused by CCI-779 treatment in mice argues that the anti-angiogenic effects of mTOR inhibitors in renal carcinoma are mediated primarily through direct effects on tumor cells. This mechanistic understanding provides rationale for exploring combination therapy using mTOR and VEGF/VEGFR pathway inhibitors in renal cancer to block the HIF pathway at distinct critical nodes (FIG. 6)

Prior work has shown that PI3 kinase/AKT pathway-driven transformation is mTOR-dependent because mTOR is a critical component of a downstream kinase cascade. This result is consistent with the broader notion of "pathway addiction" to explain why tumor cells may have a competitive disadvantage, when confronted with a pathway-specific kinase inhibitor, compared to normal cells (see, e.g. Weinstein, I. B. Science 297, 63-4 (2002)). Here we provide evidence for kinase dependence through a conceptually distinct mechanism. In renal cell carcinoma caused by VHL loss, the critical role of mTOR is not through downstream transduction of the oncogenic signal mediated through HIF. Rather, translation of HIF mRNA is TOR-dependent due to the presence of upstream regulatory signals in the 5' untranslated region. This model predicts for a highly favorable therapeutic index because decreased HIF translation in normal tissues should be inconsequential, since HIF protein is already rapidly degraded through VHL. A similar mechanism might also be responsible for clinical activity of CCI-779 in mantle cell lymphoma where the driving oncogenic lesion is presumed to be cyclin D1. Translation of the cyclin D1 mRNA, which is produced at increased levels as a consequence of the Bcl-1 translocation that defines these tumors, has also been shown to be mTOR-dependent in certain systems (see, e.g. Rowinsky, E. K. Curr Opin Oncol 16, 564-75 (2004)). Future clinical trials of mTOR inhibitors may benefit from these distinct conceptual mechanisms of mTOR dependency.

Methods

DNA Constructs and PCR Primers.

The pCSUVCG (U6-shRNA-VHL-CMV-GFP) was constructed by ligating the BamHI/EcoRI digests of pCSCG and the U6-shRNA-VHL PCR product (see, e.g. Chen, C. D. et al. Nat Med 10, 33-9 (2004)). The U6-shRNA-VHL PCR was performed using a hU6-containing plasmid at an annealing temperature of 60° C. with the primers 5' abc 3' and 5' xyz 3'. Native 5' UTR of HIF-1α was identified using Genebrowser, which contains previously identified TOP sequences (see, e.g. Laughner et al., Mol Cell Biol 21, 3995-4004 (2001)). Using human fetal brain cDNA (Marathon, Invitrogen) as template, a 387-bp fragment containing 268 base pairs of the 5'UTR and 119 base pairs of the coding region was generated using the primers 5'GGGAGATCTGGGGACAGGAG-GATCGCC-3' (SEQ ID NO: 4) and 5'-GGGAAGCTCAT-AAAAAACTTTAGATTC-3' (SEQ ID NO: 5). The PCR product was subcloned into the PCR 2.1 TA cloning vector, verified by sequencing and subsequently cleaved with Bgl II and ligated into the Bgl II site of the MSCV-puro-HIF-1α cDNA, to create the HIF-1α 5'TOP chimeric gene. The prolyl hydroxylation defective mutants of p-Babe-puro-HA-HIF-1α (P564A) and HIF-2α (P405A; P531A) were a generous gift from Dr. W. G. Kaelin.

Immunoblot Analysis and VEGF ELISA.

Cells and xenograft tumors were lysed in ECB lysis buffer or high-detergent buffer (2% SDS), respectively, supplemented with complete protease and phosphatase inhibitor cocktails (Calbiochem). Protein extracts were resolved by SDS-PAGE and transferred to nitrocellulose membranes. After blocking in Tris-buffeted saline (TBS) with 5% non-fat milk, the membranes were probed with following: anti-VHL mouse monoclonal antibody (1:400, Oncogene Research Sciences), anti-HIF1α mouse monoclonal antibody (1:250, BD Pharmingen), anti-HIF-2α mouse monoclonal antibody (1:500, Novus Biologicals), anti-GLUT-1 rabbit polyclonal antibody (1:1000, Alpha Diagnostic), anti-CA-IX rabbit polyclonal antibody (1:500, Novus Biologicals), anti-phospho-eIF4G-S1108 rabbit polyclonal antibody (1:1000, Cell Signaling), anti-phospho-S6 Ribosomal protein S235/236 rabbit polyclonal antibody (1:1000, Cell Signaling) or anti-β-actin mouse monoclonal antibody (1:5000, Sigma), diluted in TBS with 4% BSA. Bound antibody was detected using enhanced chemiluminescence (ECL, Amersham). For VEGF ELISA quantification, cells were plated in 6 well plates ($1\times10^5$ per well). Experiments were performed in triplicate. Once the cells attached, the media was changed and either 10 nM of CCI-779 or vehicle (100% ethanol) was added. Thirty-six hours later, VEGF ELISA (R&D Systems) was performed according to the manufacturer's instructions, using a Fisher Plate reader. For normalization, the VEGF protein levels were divided by the intracellular protein concentrations within each sample In Vitro and In Vivo Growth Experiments.

SN12C and ACHN (NCI60, DTP) were maintained in Dulbecco's modified Eagle's Medium (DMEM) supplemented with 10% FBS. SN12C-CSCG, ACHN-CSCG, SN12C-CSCG-VHL shRNA and ACHN-CSCG-VHL shRNA were derived by infecting cells with the pCSCG or pCSUVCG lentivirus respectively, without selection (>90% infection). Retroviruses containing the HIF1 and HIF-2 mutants (i.e. p-Babe-puro-HA-HIF-1α (P564A) and HIF-2α (P405A; P531A)) or the backbone vector were transfected into Phoenix packaging cell line using Lipofectamine 2000 (Invitrogen) according to the manufacturer's instruction. Tissue culture supernatant was harvested 48 hours later, passed through a 0.45μ filter and added to the SN12C-CSCG-VHL shRNA cells in the presence of 4 ug/ml polybrene. Infected cells were selected by growth in the presence of puromycin (1.5 ug/ml). For in vitro experiments, cells ($5\times10^4$) were plated and treated with 1 and 10 nM CCI-779 (kind gift of J. Gibbons, Wyeth) or vehicle (ethanol). On day 5-post treatment, cells were trypsinized, resuspended in DMEM with 10% FBS and counted using the VI-Cell XR automated cell viability analyzer (Beckmann Coulter). Cell counts were done in triplicate and repeated on at least 3 independent occasions. In vivo tumorigenicity was measured by injection of $5\times10^5$ SN12C-CSCG, ACHN-CSCG, SN12C-CSCG-VHL shRNA, ACHN-CSCG-VHL shRNA, SN12C-CSCG-VHL shRNA-pBABE, SN12C-CSCG-VHL shRNA-pBABE-HA-HIF-2α (P405A; P531A) cells in 100 μl of Matrigel (Collaborative Biomedical) subcutaneously into the flanks of SCID mice. Tumor size were measured weekly in three dimensions using calipers as described. When tumors reached 200 mm³, all tumors received 0.1 mg/kg/daily of CCI-779 or vehicle. All mouse experiments were performed in compliance with the guidelines of the Animal Research Committee of the University of California at Los Angeles.

Immunohistochemistry.

Xenograft tumor samples were fixed in 10% buffered formalin and embedded in paraffin. Thin sections (4 μm) were stained with hematoxylin and eosin according to standard protocols. Detection of CD-31 (1:500, Santa Cruz) and anti-VEGF rabbit polyclonal antibody (1:1000, Santa Cruz) was by standard avidin-biotin immunoperoxidase methods, with diaminobenzidine used as the chromogen and hematoxylin as the counter stain. Microvessel density was determined by light microscopy in areas of the xenograft tumor containing highest numbers of capillaries and small venules (microvessels) pet area (i.e. neovascular "hotspots") by scanning the tumor sections at low power (40× and 100×) (see, e.g. Weidner, N. et al. J Natl Cancer Inst 84, 1875-87 (1992)). Any endothelial cell or endothelial cell cluster positive for CD-31 and clearly separate from an adjacent cluster was considered to be a single, countable microvessel and results were expressed as the highest number of microvessels identified within any single 200× field. Statistical analysis was performed using the Microsoft Excel Student T-test.

Real-Time Quantitative Reverse Transcriptase-Polymerase Chain Reaction.

Total RNA was extracted from SN12C-CSCG, ACHN-CSCG, SN12C-CSCG-VHLshRNA and ACHN-CSCG-VHL shRNA cell lines treated with vehicle or 10 nM of CCI-779 using the RNeasy kit (Qiagen). Two μg of total RNA was used as a template for the production of c DNA through reverse transcription. The reactions were assembled as in a 25 μl final volume as follows: 1 μM primers (random hexamers; Invitrogen), 10 mM DTT, 1X Superscript II buffer, 0.5 μM of dATP, dCTP, dGTP and dTTP, 10U RNasin, 200 units of Superscript II reverse transcriptase. Each RNA template, primer and nuclease free water were combined and incubated for 10 minutes, then placed in an ice bath. The remaining reaction components were added and each reaction was incubated at 25° C. for 10 minutes, then 42° C. for 60 minutes and finally 70° C. for 15 minutes. Negative control reactions (which contained no RT enzyme) were also assembled. Real-time PCR was performed on an ABI Prism 7700 sequence detector (Applied Biosystems). Primers and specific probes for HIF-1α and 18S were obtained from Assays-on Demand Gene Expression products (Applied Biosystems). PCR reaction was performed as follows: 50° C. for 2 minutes, 95° C. for 10 minutes, and 40 cycles of two-step PCR (95° C. for 15 seconds and 60° C. for 1 minute). Threshold cycles (Ct's) for the RT samples were recorded. Each sample was run in duplicate. Micro-PET imaging. 2-((Kaelin et al., Trends Genet 14, 423-6 (1998))F)fluoro-2-deoxy-D-glucose (FDG) was synthesized using standard method (see, e.g. Satyamurthy et al., Imaging Biol 4, 65-70 (2002)). PET scans were conducted with the microPET Primate 4-ring system (P4; Concorde Microsystems, Knoxville, Tenn.) as previously described. CCI-779 was administered intraperitoneally at a dose of 0.1 mg/kg every 12 hours. Mice were injected intravenously with FDG (7.4 MBq) and imaged one hour after tracer injection for 15 minutes. For image reconstruction, list mode data were first sorted into 3-dimensional (3D) sinograms, followed by Fourier rebinning and 2D Filtered Back-Projection (FBP) reconstruction using a Ramp filter with one half of the Nyquist frequency as the cut-off frequency. The reconstructed spatial image resolution is ~2.2 mm. For image analysis, regions of interest (ROI) were manually placed around the tumor and the liver on transaxial images. The tumor ROI was defined in the slice with maximum tracer uptake; the liver ROI was placed in the slice with the largest cross-sectional area of the hepatic blood pool. Tracer uptake by the tumors was expressed as the ratio between the maximum intratumoral and mean hepatic counts/pixel. All quantitative values are reported as mean±standard error of the mean (SEM).

TABLES

Information provided below including sequences identified by accession number is hereby incorporated by reference.

Von Hippel-Lindau disease tumor suppressor (pVHL) (G7 protein).
LOCUS P40337 213 aa linear
ACCESSION P40337
NCBI INFORMATION: LOCUS AF010238 14543 bp DNA linear PRI 24 Nov. 2000 DEFINITION Homo sapiens von Hippel-Lindau tumor suppressor (VHL) gene, complete cds.
ACCESSION AF010238 U19763 U49746 U68055 U68176

(SEQ ID NO: 1)
MPRRAENWDEAEVGAEEAGVEEYGPEEDGGEESGAEESGPEESGPEELGA

EEEMEAGRPRPVLRSVNSREPSQVIFCNRSPRVVLPVWLNFDGEPQPYPT

LPPGTGRRIHSYRGHLWLFRDAGTHDGLLVNQTELFVPSLNVDGQPIFAN

ITLPVYTLKERCLQVVRSLVKPENYRRLDIVRSLYEDLEDHPNVQKDLER

LTQERIAHQRMGD

Hypoxia-inducible factor 1 alpha (HIF-1 alpha) (HIF1 alpha) (ARNT interacting protein) (Member of PAS protein 1) (MOP1).
LOCUS Q16665 826 aa linear
ACCESSION Q16665

(SEQ ID NO: 2)
MEGAGGANDKKKISSERRKEKSRDAARSRRSKESEVFYELAHQLPLPHNV

SSHLDKASVMRLTISYLRVRKLLDAGDLDIEDDMKAQMNCFYLKALDGFV

MVLTDDGDMIYISDNVNKYMGLTQFELTGHSVFDFTHPCDHEEMREMLTH

RNGLVKKGKEQNTQRSFFLRMKCTLTSRGRTMNIKSATWKVLHCTGHIHV

YDTNSNQPQCGYKKPPMTCLVLICEPIPHPSNIEIPLDSKTFLSRHSLDM

KFSYCDERITELMGYEPEELLGRSIYEYYHALDSDHLTKTHHDMFTKGQV

TTGQYRMLAKRGGYVWVETQATVIYNTKNSQPQCIVCVNYVVSGIIQHDL

IFSLQQTECVLKPVESSDMKMTQLFTKVESEDTSSLFDKLKKEPDALTLL

APAAGDTIISLDFGSNDTETDDQQLEEVPLYNDVMLPSPNEKLQNINLAM

SPLPTAETPKPLRSSADPALNQEVALKLEPNPESLELSFTMPQIQDQTPS

PSDGSTRQSSPEPNSPSEYCFYVDSDMVNEFKLELVEKLFAEDTEAKNPF

STQDTDLDLEMLAPYIPMDDDFQLRSFDQLSPLESSSASPESASPQSTVT

VFQQTQIQEPTANATTTTATTDELKTVTKDRMEDIKILIASPSPTHIHKE

TTSATSSPYRDTQSRTASPNRAGKGVIEQTEKSHPRSPNVLSVALSQRTT

VPEEELNPKILALQNAQRKRKMEHDGSLFQAVGIGTLLQQPDDHAATTSL

SWKRVKGCKSSEQNGMEQKTIILIPSDLACRLLGQSMDESGLPQLTSYDC

EVNAPIQGSRNLLQGEELLRALDQVN

LOCUS NP_851397 735 aa linear PRI 27 Oct. 2004 DEFINITION hypoxia-inducible factor 1, alpha subunit isoform 2 (Homo sapiens). ACCESSION NP_851397

(SEQ ID NO: 3)
MEGAGGANDKKKISSERRKEKSRDAARSRRSKESEVFYELAHQLPLPHNV

SSHLDKASVMRLTISYLRVRKLLDAGDLDIEDDMKAQMNCFYLKALDGFV

MVLTDDGDMIYISDNVNKYMGLTQFELTGHSVFDFTHPCDHEEMREMLTH

RNGLVKKGKEQNTQRSFFLRMKCTLTSRGRTMNIKSATWKVLHCTGHIHV

YDTNSNQPQCGYKKPPMTCLVLICEPIPHPSNIEIPLDSKTFLSRHSLDM

-continued
KFSYCDERITELMGYEPEELLGRSIYEYYHALDSDHLTKTHHDMFTKGQV

TTGQYRMLAKRGGYVWVETQATVIYNTKNSQPQCIVCVNYVVSGIIQHDL

IFSLQQTECVLKPVESSDMKMTQLFTKVESEDTSSLFDKLKKEPDALTLL

APAAGDTIISLDFGSNDTETDDQQLEEVPLYNDVMLPSPNEKLQNINLAM

SPLPTAETPKPLRSSADPALNQEVALKLEPNPESLELSFTMPQIQDQTPS

-continued
PSDGSTRQSSPEPNSPSEYCFYVDSDMVNEFKLELVEKLFAEDTEAKNPF

STQDTDLDLEMLAPYIPMDDDFQLRSFDQLSPLESSSASPESASPQSTVT

VFQQTQIQEPTANATTTTATTDELKTVTKDRMEDIKILIASPSPTHIHKE

TTSATSSPYRDTQSRTASPNRAGKGVIEQTEKSHPRSPNVLSVALSQRTT

VPEEELNPKILALQNAQRKRKMEHDGSLFQAVGII

---

What is claimed is:

1. A method for identifying a mammalian kidney tumor cell lineage that is likely to respond, or is responsive to an mTOR polypeptide inhibitor, the method comprising examining cells of the mammalian kidney tumor cell lineage for:

an at least 50% decrease in the expression of the Von Hippel Lindau (VHL) tumor suppressor protein (SEQ ID NO: 1) in the cells of the mammalian kidney tumor cell lineage as compared to a control cell of the same cellular lineage as the cells of the mammalian kidney tumor cell lineage;

wherein:

an at least 50% decrease in the expression of the Von Hippel Lindau (VHL) tumor suppressor protein identifies the cells of the mammalian kidney tumor cell lineage as likely to respond or responsive to an mTOR polypeptide inhibitor; and the method further comprises combining the cells of the mammalian kidney tumor cell lineage identified as likely to respond or responsive to an mTOR polypeptide inhibitor with an mTOR polypeptide inhibitor.

2. The method of claim 1, wherein a decrease in the expression of the Von Hippel Lindau (VHL) tumor suppressor protein (SEQ ID NO: 1) is examined by a method comprising observing an at least 50% decrease in the expression of mRNA encoding the Von Hippel Lindau (VHL) tumor suppressor protein (SEQ ID NO: 1).

3. The method of claim 2, wherein the method uses a polynucleotide that hybridizes to mRNA encoding the Von Hippel Lindau (VHL) tumor suppressor protein (SEQ ID NO: 1).

4. The method of claim 3, wherein the method comprises polymerase chain reaction (PCR) method or a Northern blot method.

5. The method of claim 1, wherein the mTOR inhibitor is rapamycin, SDZ-RAD, CCI-779, RAD 001, or AP23573.

6. A method for identifying a mammalian kidney tumor cell lineage that is likely to respond, or is responsive to an mTOR polypeptide inhibitor, the method comprising examining cells of the mammalian kidney tumor cell lineage for:

an at least 50% decrease in the expression of the Von Hippel Lindau (VHL) tumor suppressor protein (SEQ ID NO: 1) in the cells of the mammalian kidney tumor cell lineage as compared to a control cell of the same cellular lineage as the cells of the mammalian kidney tumor cell lineage;

wherein an at least 50% decrease in the expression of the Von Hippel Lindau (VHL) tumor suppressor protein identifies the cells of the mammalian kidney tumor cell lineage as likely to respond or responsive to an mTOR polypeptide inhibitor; and the method further comprises the use of a positron emission tomography apparatus to identify the cells of the mammalian kidney tumor cell lineage as likely to respond or responsive to an mTOR polypeptide inhibitor.

* * * * *

SEQUENCE LISTING

<160> NUMBER OF SEQ ID NOS: 5

<210> SEQ ID NO 1
<211> LENGTH: 213
<212> TYPE: PRT
<213> ORGANISM: Homo sapiens

<400> SEQUENCE: 1

Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
            20                  25                  30

Ser Gly Ala Glu Glu Ser Gly Pro Glu Glu Ser Gly Pro Glu Glu Leu
        35                  40                  45

Gly Ala Glu Glu Glu Met Glu Ala Gly Arg Pro Arg Pro Val Leu Arg
    50                  55                  60

Ser Val Asn Ser Arg Glu Pro Ser Gln Val Ile Phe Cys Asn Arg Ser
65                  70                  75                  80

Pro Arg Val Val Leu Pro Val Trp Leu Asn Phe Asp Gly Glu Pro Gln
                85                  90                  95

Pro Tyr Pro Thr Leu Pro Pro Gly Thr Gly Arg Arg Ile His Ser Tyr
            100                 105                 110

Arg Gly His Leu Trp Leu Phe Arg Asp Ala Gly Thr His Asp Gly Leu
        115                 120                 125

Leu Val Asn Gln Thr Glu Leu Phe Val Pro Ser Leu Asn Val Asp Gly
    130                 135                 140

Gln Pro Ile Phe Ala Asn Ile Thr Leu Pro Val Tyr Thr Leu Lys Glu
145                 150                 155                 160

Arg Cys Leu Gln Val Val Arg Ser Leu Val Lys Pro Glu Asn Tyr Arg
                165                 170                 175

Arg Leu Asp Ile Val Arg Ser Leu Tyr Glu Asp Leu Glu Asp His Pro
            180                 185                 190

Asn Val Gln Lys Asp Leu Glu Arg Leu Thr Gln Glu Arg Ile Ala His
        195                 200                 205

Gln Arg Met Gly Asp
    210

<210> SEQ ID NO 2
<211> LENGTH: 826
<212> TYPE: PRT
<213> ORGANISM: Homo sapiens

<400> SEQUENCE: 2

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

-continued

```
Glu Ser Glu Val Phe Tyr Glu Leu Ala His Gln Leu Pro Leu Pro His
         35                  40                  45
Asn Val Ser Ser His Leu Asp Lys Ala Ser Val Met Arg Leu Thr Ile
 50                  55                  60
Ser Tyr Leu Arg Val Arg Lys Leu Leu Asp Ala Gly Asp Leu Asp Ile
 65                  70                  75                  80
Glu Asp Asp Met Lys Ala Gln Met Asn Cys Phe Tyr Leu Lys Ala Leu
                 85                  90                  95
Asp Gly Phe Val Met Val Leu Thr Asp Asp Gly Asp Met Ile Tyr Ile
                100                 105                 110
Ser Asp Asn Val Asn Lys Tyr Met Gly Leu Thr Gln Phe Glu Leu Thr
            115                 120                 125
Gly His Ser Val Phe Asp Phe Thr His Pro Cys Asp His Glu Glu Met
        130                 135                 140
Arg Glu Met Leu Thr His Arg Asn Gly Leu Val Lys Lys Gly Lys Glu
145                 150                 155                 160
Gln Asn Thr Gln Arg Ser Phe Phe Leu Arg Met Lys Cys Thr Leu Thr
                165                 170                 175
Ser Arg Gly Arg Thr Met Asn Ile Lys Ser Ala Thr Trp Lys Val Leu
            180                 185                 190
His Cys Thr Gly His Ile His Val Tyr Asp Thr Asn Ser Asn Gln Pro
        195                 200                 205
Gln Cys Gly Tyr Lys Lys Pro Pro Met Thr Cys Leu Val Leu Ile Cys
    210                 215                 220
Glu Pro Ile Pro His Pro Ser Asn Ile Glu Ile Pro Leu Asp Ser Lys
225                 230                 235                 240
Thr Phe Leu Ser Arg His Ser Leu Asp Met Lys Phe Ser Tyr Cys Asp
                245                 250                 255
Glu Arg Ile Thr Glu Leu Met Gly Tyr Glu Pro Glu Glu Leu Leu Gly
            260                 265                 270
Arg Ser Ile Tyr Glu Tyr Tyr His Ala Leu Asp Ser Asp His Leu Thr
        275                 280                 285
Lys Thr His His Asp Met Phe Thr Lys Gly Gln Val Thr Thr Gly Gln
    290                 295                 300
Tyr Arg Met Leu Ala Lys Arg Gly Gly Tyr Val Trp Val Glu Thr Gln
305                 310                 315                 320
Ala Thr Val Ile Tyr Asn Thr Lys Asn Ser Gln Pro Gln Cys Ile Val
                325                 330                 335
Cys Val Asn Tyr Val Val Ser Gly Ile Ile Gln His Asp Leu Ile Phe
            340                 345                 350
Ser Leu Gln Gln Thr Glu Cys Val Leu Lys Pro Val Glu Ser Ser Asp
        355                 360                 365
Met Lys Met Thr Gln Leu Phe Thr Lys Val Glu Ser Glu Asp Thr Ser
    370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                405                 410                 415
Asp Thr Glu Thr Asp Asp Gln Gln Leu Glu Glu Val Pro Leu Tyr Asn
            420                 425                 430
Asp Val Met Leu Pro Ser Pro Asn Glu Lys Leu Gln Asn Ile Asn Leu
        435                 440                 445
```

```
Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 3
<211> LENGTH: 735
<212> TYPE: PRT
<213> ORGANISM: Homo sapiens
```

<400> SEQUENCE: 3

```
Met Glu Gly Ala Gly Ala Asn Asp Lys Lys Ile Ser Ser Glu
  1               5                  10                  15
Arg Arg Lys Glu Lys Ser Arg Asp Ala Ala Arg Ser Arg Arg Ser Lys
                 20                  25                  30
Glu Ser Glu Val Phe Tyr Glu Leu Ala His Gln Leu Pro Leu Pro His
             35                  40                  45
Asn Val Ser Ser His Leu Asp Lys Ala Ser Val Met Arg Leu Thr Ile
         50                  55                  60
Ser Tyr Leu Arg Val Arg Lys Leu Leu Asp Ala Gly Asp Leu Asp Ile
 65                  70                  75                  80
Glu Asp Asp Met Lys Ala Gln Met Asn Cys Phe Tyr Leu Lys Ala Leu
                 85                  90                  95
Asp Gly Phe Val Met Val Leu Thr Asp Asp Gly Asp Met Ile Tyr Ile
            100                 105                 110
Ser Asp Asn Val Asn Lys Tyr Met Gly Leu Thr Gln Phe Glu Leu Thr
            115                 120                 125
Gly His Ser Val Phe Asp Phe Thr His Pro Cys Asp His Glu Glu Met
            130                 135                 140
Arg Glu Met Leu Thr His Arg Asn Gly Leu Val Lys Lys Gly Lys Glu
145                 150                 155                 160
Gln Asn Thr Gln Arg Ser Phe Phe Leu Arg Met Lys Cys Thr Leu Thr
                165                 170                 175
Ser Arg Gly Arg Thr Met Asn Ile Lys Ser Ala Thr Trp Lys Val Leu
            180                 185                 190
His Cys Thr Gly His Ile His Val Tyr Asp Thr Asn Ser Asn Gln Pro
            195                 200                 205
Gln Cys Gly Tyr Lys Lys Pro Pro Met Thr Cys Leu Val Leu Ile Cys
            210                 215                 220
Glu Pro Ile Pro His Pro Ser Asn Ile Glu Ile Pro Leu Asp Ser Lys
225                 230                 235                 240
Thr Phe Leu Ser Arg His Ser Leu Asp Met Lys Phe Ser Tyr Cys Asp
                245                 250                 255
Glu Arg Ile Thr Glu Leu Met Gly Tyr Glu Pro Glu Glu Leu Leu Gly
            260                 265                 270
Arg Ser Ile Tyr Glu Tyr Tyr His Ala Leu Asp Ser Asp His Leu Thr
            275                 280                 285
Lys Thr His His Asp Met Phe Thr Lys Gly Gln Val Thr Thr Gly Gln
            290                 295                 300
Tyr Arg Met Leu Ala Lys Arg Gly Gly Tyr Val Trp Val Glu Thr Gln
305                 310                 315                 320
Ala Thr Val Ile Tyr Asn Thr Lys Asn Ser Gln Pro Gln Cys Ile Val
                325                 330                 335
Cys Val Asn Tyr Val Val Ser Gly Ile Ile Gln His Asp Leu Ile Phe
            340                 345                 350
Ser Leu Gln Gln Thr Glu Cys Val Leu Lys Pro Val Glu Ser Ser Asp
            355                 360                 365
Met Lys Met Thr Gln Leu Phe Thr Lys Val Glu Ser Glu Asp Thr Ser
            370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                405                 410                 415
```

```
Asp Thr Glu Thr Asp Asp Gln Gln Leu Glu Val Pro Leu Tyr Asn
                420             425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
        530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Thr Ala Thr Thr Asp Glu Leu
610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Ile
                725                 730                 735

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
gggagatctg gggacaggag gatcgcc                                          27

<210> SEQ ID NO 5
<211> LENGTH: 27
<212> TYPE: DNA
<213> ORGANISM: Artificial Sequence
```

-continued

```
<220> FEATURE:
<223> OTHER INFORMATION: primer

<400> SEQUENCE: 5
gggaagctca taaaaaactt tagattc                                        27
```